(12) United States Patent
Chun et al.

(10) Patent No.: US 10,978,173 B2
(45) Date of Patent: Apr. 13, 2021

(54) METHOD FOR REDUCING NOISE LEVEL OF DATA SET FOR A TARGET ANALYTE

(71) Applicant: SEEGENE, INC., Seoul (KR)

(72) Inventors: Jong Yoon Chun, Seoul (KR); Young Jo Lee, Seoul (KR); Han Bit Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 252 days.

(21) Appl. No.: 16/075,192

(22) PCT Filed: Feb. 3, 2017

(86) PCT No.: PCT/KR2017/001222
§ 371 (c)(1),
(2) Date: Aug. 3, 2018

(87) PCT Pub. No.: WO2017/135756
PCT Pub. Date: Aug. 10, 2017

(65) Prior Publication Data
US 2019/0122748 A1    Apr. 25, 2019

(30) Foreign Application Priority Data
Feb. 5, 2016    (KR) .................. 10-2016-0014623

(51) Int. Cl.
*G06F 17/15*    (2006.01)
*G16B 25/20*    (2019.01)
(Continued)

(52) U.S. Cl.
CPC .............. *G16B 25/20* (2019.02); *C12Q 1/686* (2013.01); *C12Q 1/6851* (2013.01); *G06F 17/15* (2013.01);
(Continued)

(58) Field of Classification Search
USPC ......................................................... 702/191
See application file for complete search history.

(56) References Cited

U.S. PATENT DOCUMENTS 6,087,182 A * 7/2000 Jeng ........................ G01N 21/05
356/72
7,363,168 B2 * 4/2008 Taylor .................. C12Q 1/6851
435/6.16
(Continued)

OTHER PUBLICATIONS

Mehndiratta et al., (2008) "Fluorescence acquisition during hybridization phase in quantitative real-time PCR improves specificity and signal-to-noise ratio.", BioTechniques, vol. 45, No. 6, pp. 625-634.
(Continued)

*Primary Examiner* — Paul D Lee
(74) *Attorney, Agent, or Firm* — Harness, Dickey & Pierce, P.L.C.

(57) ABSTRACT

The present invention relates to a method for reducing a noise level of a data set for a target analyte in a sample. The present invention can reduce a noise level of a data set to a proper level conveniently by applying a noise-reduction ratio to the data set thereby the possibility of false positive may be reduced effectively. According to the present invention, the calibrated data set is obtained by using the noise-reduction ratio, so that the noise level of a data set is reduced without change of signal ratio between the data point in the data set.

15 Claims, 15 Drawing Sheets

(51) Int. Cl.
  *C12Q 1/686* (2018.01)
  *G16B 20/20* (2019.01)
  *C12Q 1/6851* (2018.01)
  *G16B 40/10* (2019.01)
(52) U.S. Cl.
  CPC ............. *G16B 20/20* (2019.02); *G16B 40/10* (2019.02); *C12Q 2537/165* (2013.01)

(56) References Cited

U.S. PATENT DOCUMENTS

| | | | | |
|---|---|---|---|---|
| 2006/0271308 A1* | 11/2006 | Lerner | ................. | G06K 9/0053 702/19 |
| 2007/0179367 A1* | 8/2007 | Ruchti | ................. | A61B 5/1495 600/310 |
| 2008/0154511 A1 | 6/2008 | Leong | | |
| 2012/0245447 A1* | 9/2012 | Karan | .................... | G16H 40/63 600/365 |
| 2014/0106978 A1* | 4/2014 | Woo | ....................... | G16B 25/00 506/9 |
| 2015/0368702 A1* | 12/2015 | Gunstream | ........ | G01N 21/6486 435/6.12 |
| 2016/0161406 A1* | 6/2016 | Kim | ....................... | G01N 21/59 436/501 |

OTHER PUBLICATIONS

International Search Report (ISR) from corresponding PCT Application No. PCT/KR2017/001222 dated May 22, 2017.

Written Opinion of the International Searching Authority from corresponding PCT Application No. PCT/KR2017/001222 dated May 22, 2017.

Extended European Search Report from corresponding European Patent Application No. 17747801.3, dated Sep. 23, 2019.

Spiess A N et al: "Impact of Smoothing on Parameter Estimation in Quantitative DNA Amplification Experiments", Clinical Chemistry, vol. 61, No. 2, Dec. 4, 2014 (Dec. 4, 2014), pp. 379-388.

Spiess A N et al: "Supporting Information. Impact of Smoothing on Parameter Estimation in Quantitative DNA Amplification Experiments", Dec. 4, 2014 (Dec. 4, 2014). Retrieved from the Internet: URL:http://clinchem.aaccjnls.org/highwire/filestream/2979/field_highwire_adjunct_files/0/clinchem.2014.230656-1.pdf <https://protect-us.mimecast.com/s/GkmkC5yIQVT0IQLnuzlyrx>.

* cited by examiner

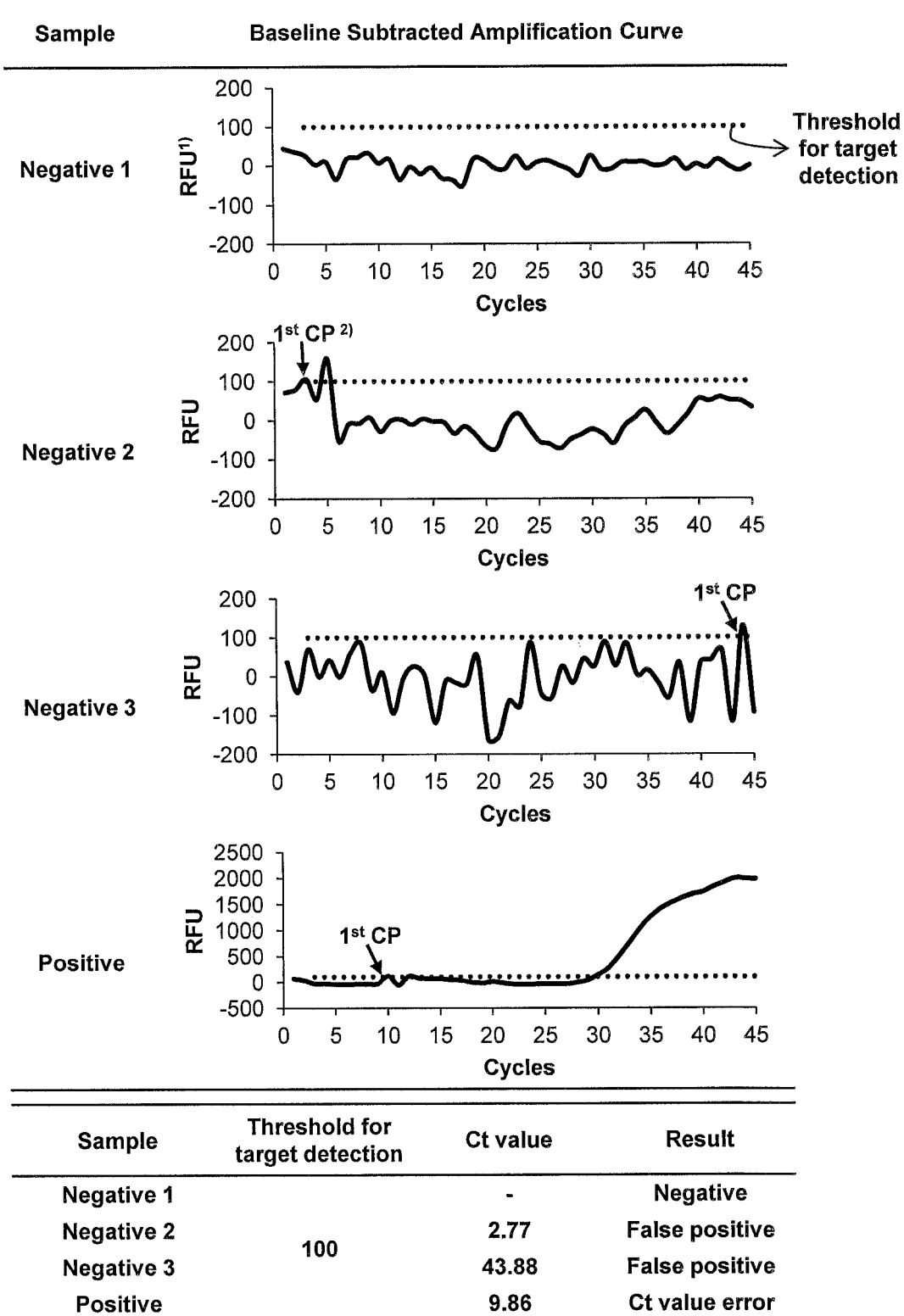

| Data set | Noise-level determining region | RFU Maximum RFU | RFU Minimum RFU | ΔRFU | Noise-reduction goal value (ΔRFU) | N-Ratio[3] |
|---|---|---|---|---|---|---|
| Before Calibration | 5-10 cycles | 86 | -35 | 121 | 80 | 1.51 |
| After Calibration | | 57 | -23 | 80 | | 1.00 |

[1] RFU represents relative fluorescence units.
[2] cRFU represents calibrated relative fluorescence units.
[3] N-Ratio represents the noise-reduction ratio.

1) RFU represents relative fluorescence units.
2) cRFU represents calibrated relative fluorescence units.
3) 1st CP represents the first crossing point between RFU and Threshold for target detection.

1) RFU represents relative fluorescence units.
2) cRFU represents calibrated relative fluorescence units.
3) N-Ratio represents the noise-reduction ratio.

1) RFU represents relative fluorescence units.
2) cRFU represents calibrated relative fluorescence units.
3) 1st CP represents the first crossing point between RFU and Threshold for target detection.

1) RFU represents relative fluorescence units.
2) cRFU represents calibrated relative fluorescence units.
3) N-DV represents the noise-reduction determinative value.
4) N-GV represents the noise-reduction goal value.
5) N-Ratio represents the noise-reduction ratio.

1) RFU represents relative fluorescence units.
2) cRFU represents calibrated relative fluorescence units.
3) N-DV represents the noise-reduction determinative value.
4) N-GV represents the noise-reduction goal value.
5) N-Ratio represents the noise-reduction ratio.

1) RFU represents relative fluorescence units.
2) cRFU represents calibrated relative fluorescence units.
3) 1st CP represents the first crossing point between RFU and Threshold for target detection.

1) RFU represents relative fluorescence units.
2) cRFU represents calibrated relative fluorescence units.
3) 1st CP represents the first crossing point between RFU and Threshold for target detection.

1) RFU represents relative fluorescence units.
2) cRFU represents calibrated relative fluorescence units.
3) N-Th represents the threshold for noise analysis.
4) N-GV represents the noise-reduction goal value.
5) N-Ratio represents the noise-reduction ratio.

1) RFU represents relative fluorescence units.
2) cRFU represents calibrated relative fluorescence units.
3) N-Th represents the threshold for noise analysis.
4) N-GV represents the noise-reduction goal value.
5) N-Ratio represents the noise reduction ratio.

1) RFU represents relative fluorescence units.
2) cRFU represents calibrated relative fluorescence units.
3) 1st CP represents the first crossing point between RFU and Threshold for target detection.

[1] RFU represents relative fluorescence units.
[2] cRFU represents calibrated relative fluorescence units.
[3] 1st CP represents the first crossing point between RFU and Threshold for target detection.

METHOD FOR REDUCING NOISE LEVEL OF DATA SET FOR A TARGET ANALYTE

CROSS-REFERENCE TO RELATED APPLICATIONS

This application is a national phase application of PCT Application No. PCT/KR2017/001222, filed on 3 Feb. 2017, which claims priority to Korean Patent Application No. 10-2016-0014623 filed on Feb. 5, 2016. The entire disclosures of the applications identified in this paragraph are incorporated herein by reference.

FIELD OF THE INVENTION

The present invention relates to a method for reducing a noise level of a data set for a target analyte in a sample.

BACKGROUND OF THE INVENTION

A polymerase chain reaction (hereinafter referred to as "PCR") which is most widely used for the nucleic acid amplification includes repeated cycles of denaturation of double-stranded DNA, followed by oligonucleotide primer annealing to the DNA template, and primer extension by a DNA polymerase (Mullis et al., U.S. Pat. Nos. 4,683,195, 4,683,202 and 4,800,159; Saiki et al., (1985) Science 230, 1350-1354).

A real-time polymerase chain reaction is one of PCR-based technologies for detecting a target nucleic acid molecule in a sample in a real-time manner. For detecting a specific target nucleic acid molecule, the real-time PCR uses a signal-generating means for generating a fluorescence signal being detectable in a proportional manner to the amount of the target molecule. The generation of fluorescence signals may be accomplished by using either intercalators generating signals when intercalated between double-stranded DNA or oligonucleotides carrying fluorescence reporter and quencher molecules. The fluorescence signals whose intensities are proportional to the amount of the target molecule are detected at each amplification cycle and plotted against amplification cycles, whereby an amplification curve or amplification profile curve is obtained.

The generation of noise signals is one of serious shortcomings of real-time PCR technologies. Non-specific noise signals generated regardless of the presence of the target nucleic acid molecule are likely to result in a false positive detection.

The noise signal may be generated by various causes. For example, the noise signal may be generated by micro bubbles or particulates in a reaction mixture, contamination of cover film for reaction tube, errors in luminescence system e.g., light source and lens, electrical noise in power system, temperature or other biochemical problems.

The pattern of noise signal may be various depending on the causes, for example, a strong noise signal may be generated then disappeared within one or two cycles or may be a non-specific noise signal may be added to the target signal throughout the entire cycles.

These noise signals may be a cause of false positive result of target nucleic acid molecule detection test. Therefore, various approaches for detecting and eliminating the noise signal have been developed. For example, a signal increased more than a specific threshold between the cycles may be determined as a noise signal (U.S. Pat. No. 8,560,247); an outlier signal may be determined as a noise signal by applying a statistical test with an approximation of the calculated curve for a data set of an amplification reaction and calibrated to fit the calculated curve (U.S. Pat. No. 7,668,663); and a noise signal may be determined by calculating the residual between linear fitted data set or smoothed data set and original data set (U.S. Pat. No. 7,647,187).

These published methods that selectively calibrate signals of data points expected to include noise signals have drawbacks that they may not eliminate non-specific noise signals generated throughout the entire cycles. Moreover, because the conventional methods calibrate only a signal of the cycle which meets the noise criteria a signal ratio between data point regions calibrated and not calibrated is very likely to be changed. Therefore, there is a need in the art to develop a novel calibration method which is capable of reliably reducing the overall noise-level of a data set.

Throughout this application, various patents and publications are referenced and citations are provided in parentheses. The disclosure of these patents and publications in their entirety are hereby incorporated by references into this application in order to more fully describe this invention and the state of the art to which this invention pertains.

SUMMARY OF THE INVENTION

The present inventors have made intensive researches to develop novel approaches for more effectively and reliably reducing a signal noise generated in the detection of signals for a target nucleic acid molecule. As a result, we have found that when a noise-reduction ratio provided by using (i) a noise-reduction goal value and (ii) a value provided by signal values of data points within a noise-level determining region is applied to signal values of a plurality of data points of a data set, the signal noise level is reduced more effectively and reliably so that the accuracy of the analysis result would be improved.

Accordingly, it is an object of this invention to provide a method for reducing a noise level of a data set for target analyte in a sample.

It is another object of this invention to provide a computer readable storage medium containing instructions to configure a processor to perform a method for reducing a noise level of a data set for target analyte in a sample.

It is still another object of this invention to provide a device for reducing a noise level of a data set for target analyte in a sample.

It is still another object of this invention to provide a computer program to be stored on a computer readable storage medium to configure a processor to perform a method for reducing a noise level of a data set for target analyte in a sample.

Other objects and advantages of the present invention will become apparent from the detailed description to follow taken in conjugation with the appended claims and drawings.

BRIEF DESCRIPTION OF THE DRAWINGS

FIG. 2 represents influences of a signal noise level on analysis results of a target nucleic acid molecule.

DETAILED DESCRIPTION OF THIS INVENTION

I. Method for Reducing a Noise Level of a Data Set for Target Analyte

In one aspect of this invention, there is provided a method for reducing a noise level of a data set for target analyte in a sample comprising:

(a) providing a noise-reduction ratio for reducing a noise level of a data set; wherein the data set is obtained from a signal-generating process for the target analyte using a signal-generating means; wherein the data set comprises a plurality of data points comprising cycles of the signal-generating process and signal values at the cycles; wherein the noise-reduction ratio is provided by a value provided by signal values of data points within a noise-level determining region and a noise-reduction goal value;

(b) providing a calibrated data set having a reduced noise level by calibrating the signal values of a plurality of data point in the data set with the noise reduction ratio.

The present inventors have made intensive researches to develop novel approaches for more effectively and reliably reducing a signal noise generated in the detection of signals for a target nucleic acid molecule. As a result, we have found that when reducing ratio provided by using (i) a noise-reduction goal value and (ii) a value provided by signal values of data points within a noise-level determining region is applied to signal values of a plurality of data points of a data set, the signal noise level is reduced more effectively and reliably so that the accuracy of the analysis result would be improved.

Although the present invention is described as "a method for reducing a noise level of a data set for target analyte in a sample", it may be also described as "a method for analyzing a target analyte" or "a method for detecting a target analyte" because the data set is finally used for qualitative or quantitative detection of the target analyte in the sample.

Figure 1:
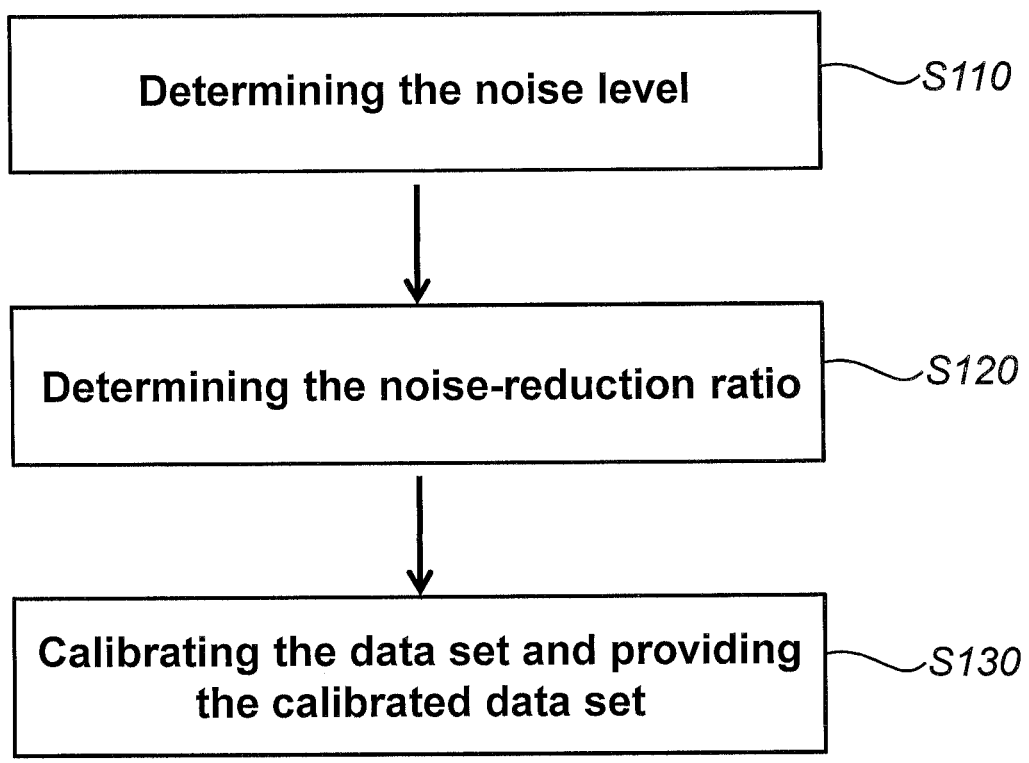
FIG. 1 represents a flow diagram illustrating an embodiment of the present method for reducing a noise level of a data set for a target analyte in a sample.

With refereeing to FIG. 1 representing a flow diagram illustrating an embodiment of the present method for reducing a noise level of a data set for a target analyte in a sample, the present invention will be described in more detail as follows:

Step (a): Providing a Noise-Reduction Ratio for Reducing a Noise Level of a Data Set (S110 and S120)

According to the present method, a noise-reduction ratio for reducing a noise level of a data set is provided. The data set is obtained from a signal-generating process for the target analyte using a signal-generating means, and the data set comprises a plurality of data points comprising cycles of the signal-generating process and signal values at the cycles. The noise-reduction ratio is provided by a value provided by signal values of data points within a noise-level determining region and a noise-reduction goal value.

The term "target analyte" as used herein may include various materials (e.g., biological materials and non-biological materials such as chemicals). Particularly, the target analyte may include biological materials such as nucleic acid molecules (e.g., DNA and RNA), proteins, peptides, carbohydrates, lipids, amino acids, biological chemicals, hormones, antibodies, antigens, metabolites and cells. More particularly, the target analyte may include nucleic acid molecules. According to an embodiment, the target analyte may be a target nucleic acid molecule.

The term used herein "sample" may include biological samples (e.g., cell, tissue and fluid from a biological source) and non-biological samples (e.g., food, water and soil). The biological samples may include virus, bacteria, tissue, cell, blood (e.g., whole blood, plasma and serum), lymph, bone marrow aspirate, saliva, sputum, swab, aspiration, milk, urine, stool, vitreous humour, sperm, brain fluid, cerebrospinal fluid, joint fluid, fluid of thymus gland, bronchoalveolar lavage, ascites and amnion fluid. When a target analyte is a target nucleic acid molecule, the sample is subjected to a nucleic acid extraction process. When the extracted nucleic acid is RNA, reverse transcription process is performed additionally to synthesize cDNA from the extracted RNA (Joseph Sambrook, et al., *Molecular Cloning, A Laboratory Manual*, Cold Spring Harbor Laboratory Press, Cold Spring Harbor, N.Y. (2001)).

The term used herein "signal-generating process" refers to any process capable of generating signals in a dependent manner on a property of a target analyte in a sample, wherein the property may be, for instances, activity, amount or presence (or absence) of the target analyte, in particular the presence of (or the absence of) an analyte in a sample. According to an embodiment, the signal-generating process generates signals in a dependent manner on the presence of the target analyte in the sample.

Such signal-generating process may include biological and chemical processes. The biological processes may include genetic analysis processes such as PCR, real-time PCR, microarray and invader assay, immune assay processes and bacteria growth analysis. According to an embodiment, the signal-generating process includes genetic analysis processes. The chemical processes may include a chemical analysis comprising production, change or decomposition of chemical materials. According to an embodiment, the signal-generating process may be a PCR or a real-time PCR.

The signal-generating process may be accompanied with a signal change. The term "signal" as used herein refers to a measurable output. The signal change may serve as an indicator indicating qualitatively or quantitatively the property, in particular the presence or absence of a target analyte. Examples of useful indicators include fluorescence intensity, luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance. The most widely used indicator is fluorescence intensity. The signal change may include a signal decrease as well as a signal increase. According to an embodiment, the signal-generating process is a process amplifying the signal values.

The term used herein "signal-generating means" refers to any material used in the generation of a signal indicating a property, more specifically the presence or absence of the target analyte which is intended to be analyzed.

A wide variety of the signal-generating means have been known to one of skill in the art. Examples of the signal-generating means may include oligonucleotides, labels and enzymes. The signal-generating means include both labels per se and oligonucleotides with labels. The labels may include a fluorescent label, a luminescent label, a chemiluminescent label, an electrochemical label and a metal label. The label per se like an intercalating dye may serve as signal-generating means. Alternatively, a single label or an interactive dual label containing a donor molecule and an acceptor molecule may be used as signal-generating means in the form of linkage to at least one oligonucleotide. The signal-generating means may comprise additional components for generating signals such as nucleolytic enzymes (e.g., 5'-nucleases and 3'-nucleases).

Where the present method is applied to determination of the presence or absence of a target nucleic acid molecule, the signal-generating process may be performed in accordance with a multitude of methods known to one of skill in the art. The methods include TaqMan™ probe method (U.S. Pat. No. 5,210,015), Molecular Beacon method (Tyagi et al., Nature Biotechnology, 14 (3):303(1996)), Scorpion method (Whitcombe et al., Nature Biotechnology 17:804-807 (1999)), Sunrise or Amplifluor method (Nazarenko et al., Nucleic Acids Research, 25(12):2516-2521(1997), and U.S. Pat. No. 6,117,635), Lux method (U.S. Pat. No. 7,537,886), CPT (Duck P, et al., Biotechniques, 9:142-148(1990)), LNA method (U.S. Pat. No. 6,977,295), Plexor method (Sherrill C B, et al., Journal of the American Chemical Society, 126: 4550-4556(2004)), Hybeacons™ (D. J. French, et al., Molecular and Cellular Probes (2001) 13, 363-374 and U.S. Pat. No. 7,348,141), Dual-labeled, self-quenched probe (U.S. Pat. No. 5,876,930), Hybridization probe (Bernard P S, et al., Clin Chem 2000, 46, 147-148), PTOCE (PTO cleavage and extension) method (WO 2012/096523), PCE-SH (PTO Cleavage and Extension-Dependent Signaling Oligonucleotide Hybridization) method (WO 2013/115442) and PCE-NH (PTO Cleavage and Extension-Dependent Non-Hybridization) method (PCT/KR2013/012312) and CER method (WO 2011/037306). The amplification reaction of the present invention may be performed by using one of the above-described methods.

The term used herein "amplification" or "amplification reaction" refers to a reaction for increasing or decreasing signals.

According to an embodiment of this invention, the amplification reaction refers to an increase (or amplification) of a signal generated depending on the presence of the target analyte by using the signal-generating means. The amplification reaction is accompanied with or without an amplification of the target analyte (e.g., nucleic acid molecule). Therefore, according to an embodiment of this invention, the signal-generating process is performed with or without an amplification of the target nucleic acid molecule. More particularly, the amplification reaction of present invention refers to a signal amplification reaction performed with an amplification of the target analyte.

The data set obtained from an amplification reaction comprises an amplification cycle. The term used herein "cycle" refers to a unit of changes of conditions or a unit of a repetition of the changes of conditions in a plurality of measurements accompanied with changes of conditions. For example, the changes of conditions or the repetition of the changes of conditions include changes or repetition of changes in temperature, reaction time, reaction number, concentration, pH and/or replication number of a measured subject (e.g., target nucleic acid molecule). Therefore, the cycle may include a condition (e.g., temperature or concentration) change cycle, a time or a process cycle, a unit operation cycle and a reproductive cycle. A cycle number represents the number of repetition of the cycle. In this document, the terms "cycle" and "cycle number" are used interchangeably.

For example, when enzyme kinetics is investigated, the reaction rate of an enzyme is measured several times as the concentration of a substrate is increased regularly. In this reaction, the increase in the substrate concentration may correspond to the changes of the conditions and the increasing unit of the substrate concentration may correspond to a cycle. For another example, when an isothermal amplification of nucleic acid is performed, the signals of a single sample are measured multiple times with a regular interval of times under isothermal conditions. In this reaction, the reaction time may correspond to the changes of conditions and a unit of the reaction time may correspond to a cycle. According to another embodiment, as one of methods for detecting a target analyte through a nucleic acid amplification reaction, a plurality of fluorescence signals generated from the probes hybridized to the target analyte are measured with a regular change of the temperature in the reaction. In this reaction, the change of the temperature may correspond to the changes of conditions and the temperature may correspond to a cycle.

Particularly, when repeating a series of reactions or repeating a reaction with a time interval, the term "cycle" refers to a unit of the repetition. For example, in a polymerase chain reaction (PCR), a cycle refers to a reaction unit comprising denaturation of a target nucleic acid molecule, annealing (hybridization) between the target nucleic acid molecule and primers and primer extension. The increases in the repetition of reactions may correspond to the changes of conditions and a unit of the repetition may correspond to a cycle.

According to an embodiment, where the target nucleic acid molecule is present in a sample, values (e.g., intensities) of signals measured are increased or decreased upon increasing cycles of an amplification reaction. According to an embodiment, the amplification reaction to amplify signals indicative of the presence of the target nucleic acid molecule may be performed in such a manner that signals are amplified simultaneously with the amplification of the target nucleic acid molecule (e.g., real-time PCR). Alternatively, the amplification reaction may be performed in such a manner that signals are amplified with no amplification of the target nucleic acid molecule [e.g., CPT method (Duck P, et al., Biotechniques, 9:142-148 (1990)), Invader assay (U.S. Pat. Nos. 6,358,691 and 6,194,149)].

The target analyte may be amplified by various methods. For example, a multitude of methods have been known for amplification of a target nucleic acid molecule, including, but not limited to, PCR (polymerase chain reaction), LCR (ligase chain reaction, see U.S. Pat. No. 4,683,195 and No. 4683202; A Guide to Methods and Applications (Innis et al., eds, 1990); Wiedmann M, et al., "Ligase chain reaction (LCR)—overview and applications." PCR Methods and Applications 1994 February; 3(4):S51-64), GLCR (gap filling LCR, see WO 90/01069, EP 439182 and WO 93/00447), Q-beta (Q-beta replicase amplification, see Cahill P, et al., Clin Chem., 37(9):1482-5(1991), U.S. Pat. No. 5,556,751), SDA (strand displacement amplification, see G T Walker et al., Nucleic Acids Res. 20(7):1691-1696(1992), EP 497272), NASBA (nucleic acid sequence-based amplification, see Compton, J. Nature 350(6313):91-2(1991)), TMA (Transcription-Mediated Amplification, see Hofmann W P et al., J Clin Virol. 32(4):289-93(2005); U.S. Pat. No. 5,888,779).) or RCA (Rolling Circle Amplification, see Hutchison C. A. et al., Proc. Natl Acad. Sci. USA. 102:17332-17336(2005)).

According to an embodiment, the label used for the signal-generating means may comprise a fluorescence, more particularly, a fluorescent single label or an interactive dual label comprising donor molecule and acceptor molecule (e.g., an interactive dual label containing a fluorescent reporter molecule and a quencher molecule).

According to an embodiment, the amplification reaction used in the present invention may amplify signals simultaneously with amplification of the target analyte, particularly the target nucleic acid molecule. According to an embodiment, the amplification reaction is performed in accordance with a PCR or a real-time PCR.

The data set obtained from a signal-generating process comprises a plurality of data points comprising cycles of the signal-generating process and signal values at the cycles.

The term used herein "values of signals" or "signal values" means either values of signals actually measured at the cycles of the signal-generating process (e.g., actual value of fluorescence intensity processed by amplification reaction) or their modifications. The modifications may include mathematically processed values of measured signal values (e.g., intensities). Examples of mathematically processed values of measured signal values may include logarithmic values and derivatives of measured signal values. The derivatives of measured signal values may include multi-derivatives.

The term used herein "data point" means a coordinate value comprising a cycle and a value of a signal at the cycle. The term used herein "data" means any information included in data set. For example, each of cycles and signal values of an amplification reaction may be data. The data points obtained from a signal-generating process, particularly from an amplification reaction may be plotted with coordinate values in a rectangular coordinate system. In the rectangular coordinate system, the X-axis represents cycles of the amplification reaction and the Y-axis represents signal values measured at each cycles or modifications of the signal values.

The term used herein "data set" refers to a set of data points. The data set may include a raw data set which is a set of data points obtained directly from the signal-generating process (e.g., an amplification reaction) using a signal-generating means. Alternatively, the data set may be a modified data set which is obtained by a modification of the data set including a set of data points obtained directly from the signal-generating process. The data set may include an entire or a partial set of data points obtained from the signal-generating process or modified data points thereof.

According to an embodiment of this invention, the data set may be a mathematically processed data set of the raw data set. In particular, the data set may be a baseline subtracted data set for removing a background signal value from the raw data set. The baseline subtracted data set may be obtained by methods well known in the art (e.g., U.S. Pat. No. 8,560,240).

According to an embodiment, the method further comprises the step of performing the signal-generating process to obtain a data set of the target analyte in the sample before the step (a).

According to an embodiment, the data set of the target analyte may have information indicating the presence or absence of the target analyte in the sample. In this case, the method provided by the present invention is described as "a method for calibrating data set representing the presence or absence of a target analyte in a sample". The calibration of a data set representing the presence or absence of a target analyte in a sample is performed eventually for determining the presence or absence of a target analyte in a sample. The term used "determining the presence or absence of an analyte in a sample" means determining qualitatively or quantitatively the presence or absence of an analyte in a sample.

The term "noise" or "signal noise" or "noise signal" as used herein refers to an unwanted and non-analyte related signal, which is unrelated to the presence or absence of a target analyte. A noise signal may be determined by using filtered signal value or average of signal values. For example a noise may be an error signal value or an error signal variation value.

A noise level may be, for example, an amplitude, envelope or other types of magnitude of noise signal. According to an embodiment, the noise level may be determined by using signal values within a noise-level determining region.

The term used herein "noise-level determining region" means a set of data points used in determining the noise level of a data set. According to an embodiment, the noise-level determining region may be expressed as a certain range of cycles of data points included in the set of data points used in determining the noise level of the data set.

Specifically, the noise-level determining region may be an early stage of signal-generating process or a portion thereof. More specifically, when the signal-generating process is an amplification reaction (e.g. PCR), the noise-level determining region may be a background region or a portion thereof. Even more specifically, the noise-level determining region may be selected from the region of cycles of the amplification reaction, e.g., cycles 1-30, 1-20, 1-15, 1-10, 1-8, 1-7, 2-30, 2-20, 2-15, 2-10, 2-8, 2-7, 3-30, 3-20, 3-15, 3-10, 3-8, 3-7, 4-12, 5-15 or 5-10 of the data set. According to an embodiment, the start cycle of the noise-level determining region is selected from 1, 2, 3, 4, 5, 6 or 7 cycle and the end cycle is selected from 3, 4, 5, 6, 7, 8, 9, 10, 11, 12 of 13 cycle.

According to an embodiment, the noise-level determining region may comprise one or more cycles. The number of cycles in the noise-level determining region may be not less than 1, 2, 3, 4, or 5 and not more than 30, 20, 15, 12, 10, 8, 7, or 6.

The term "background signal" as used herein refers to a signal not originated from a target analyte, for example including a signal generated from an analytical instrument or a signal-generating means itself. The term "background signal region" or "background region" refers to a group of cycles of data points in which the signals of the data points in background region is composed mostly of a background signal and have little or no signal generated from a target analyte. When the noise-level determining region is set in the background region, a noise level may be measured more accurately.

The background region may be determined by various approaches. For instance, the end-point cycle of the background region may be determined with a cycle of the first data point having a slope more than a certain threshold in the first derivatives of the data set obtained by a nucleic acid amplification process. Alternatively, the end-point cycle of the background region may be determined with a starting cycle of the first peak in the first derivatives of the data set obtained by a nucleic acid amplification process. Otherwise, the end-point cycle of the background region may be determined with a cycle of a data point having a maximum curvature.

The noise level may be determined by various approaches. The noise level may be determined by using any type of values which reflect the characteristics of the signals in the noise-level determining region.

According to an embodiment, the noise-level of the data set may be determined by using at least one characteristics of signal values of the data points within the noise-level determining region selected from the group consisting of (i) a maximum; (ii) a difference between a maximum and a minimum; (iii) an average; (iv) a variance; (v) a standard deviation; and (vi) a coefficient of variation of signal values of the data points within the noise-level determining region. Specifically, the noise-level of the data set may be determined by using (i) a maximum; or (ii) a difference between a maximum and a minimum of the signal values of the data points within the noise-level determining region. More specifically, the difference between a maximum and a minimum of the signal values of the data points within the noise-level determining region may be determined by subtraction of the minimum signal value from the maximum signal value of the data points within the noise-level determining region. According to an embodiment, the noise-level is represented as a value.

The noise-reduction ratio is provided by (i) a value provided by signal values of the data points within the noise-level determining region and (ii) a noise-reduction goal value.

The noise reduction refers to reducing a signal noise level of a data set. The reduction of a signal noise level may be performed by reducing signal values of a data set by a certain ratio. Because signal values of data points in a data set are decreased by the same ratio, the ratio of signal values between the data points remains unchanged.

The reduction rate of noise level is determined by considering the noise-reduction ratio, and the noise-reduction ratio is provided by a value provided by signal values of data points within a noise-level determining region and a noise-reduction goal value. The value provided by signal values of data points within a noise-level determining region may be the noise level.

A difference between two signal values (e.g. ΔRFU) may be designated or determined as the noise-level or noise-reduction determinative value, and a signal value (e.g. RFU) may be designated or determined as the noise-reduction goal value, for example, a signal value lower than a threshold for target detection to permit a noise signal to be reduced below the threshold for target detection. In such case, the need for the noise reduction may be determined by comparing the noise level of the data set with the noise-reduction determinative value, because the noise level and the noise-reduction determinative value are a value of the same type (e.g. ΔRFU). However, the noise-reduction ratio may not be determined with the noise level and the noise-reduction goal value because the noise level is a difference between two signal values (e.g. ΔRFU) but the noise-reduction goal value is a signal value (e.g. RFU). Therefore, in this case, the noise-reduction ratio may be provided by using the noise-reduction goal value that is noise level and another value obtained from signal values of data points within the noise-level determining region that is comparable to the noise-reduction goal value.

The term used herein "noise-reduction goal value" refers to a desired value or a goal value used in determining the reduction rate of the signal noise level of a data set for a target analyte. According to the method of the present invention, the noise level in a data set may be reduced to the noise-reduction goal value.

The noise-reduction goal value may be any value capable of serving as a desired value or a goal value for noise reduction. The type or magnitude of the value capable of serving as a desired value or a goal value for noise reduction may be different depending on a signal-generating process, a signal-generating means or a target analyte. The noise-reduction goal value may be provided by using an experimentally determined value. Specifically, the noise-reduction goal value may be provided by using an experimentally obtained data set that is used for determining the noise-reducing goal value.

The data set provided for determining the noise-reduction goal value may be a data set obtained by a control signal-generating process for determining the noise-reduction goal value. Alternatively, when the signal-generating process comprises a plurality of signal-generating processes, the data set provided for determining the noise-reduction goal value may be selected from a plurality of data sets obtained from the plurality of signal-generating processes.

The control signal-generating process refers to a standard and noise-free signal-generating process performed separately from the signal-generating process for determining the target analyte in the sample. The separate control signal-generating process may be performed under the substantially same conditions as those of the signal-generating process for determining the target analyte in the sample. The control data set may be obtained from the control signal-generating process. The noise-reduction goal value may be provided by the control data set.

According to an embodiment, the noise-reduction goal value may be determined by using at least one characteristics of signal values of data points within a noise-level determining region of a data set obtained from the control signal-generating process selected from the group consisting of (i) a maximum; (ii) a difference between a maximum and a minimum; (iii) an average; (iv) a variance; (v) a standard deviation and (vi) coefficient of variation of signal values of data points within a noise level determining region of a data set obtained from the control signal-generating process. Specifically, the noise-reduction goal value may be determined by using (i) a maximum; or (ii) a difference between a maximum and a minimum of signal values of data points within a noise level determining region of a data set obtained from the control signal-generating process.

Alternatively, the noise-reduction goal value may be a value less than signal values of the data points within the noise-level determining region in the data set obtained from the signal-generating process. In this case, the noise-reduction goal value is determined in considering the purpose, sensitivity, specificity or condition of an analysis, or characteristics of analytical instruments.

According to an embodiment, when the signal-generating process comprises a plurality of signal-generating processes and the data set comprises a plurality of data sets obtained from the plurality of signal-generating processes, the noise-reduction goal values to be applied to the plurality of data sets may be identical to each other.

According to an embodiment, when the signal-generating process comprises a plurality of signal-generating processes, the noise-reduction goal value may be determined by using at least one characteristics of signal values of data points within a noise-level determining region of the data set selected from the plurality of data sets obtained from the plurality of signal-generating processes selected from the group consisting of (i) a maximum; (ii) a difference between a maximum and a minimum; (iii) an average; (iv) a variance; (v) a standard deviation and (vi) a coefficient of variation of signal values of data points within a noise-level determining region of the data set selected from the plurality of data sets obtained from the plurality of signal-generating processes. Specifically, the noise-reduction goal value may be determined by using (iii) an average or (vi) a coefficient of variation of signal values of data points within a noise-level determining region of the data set selected from the plurality of data sets obtained from the plurality of signal-generating processes.

According to an embodiment, when the signal-generating process comprises a plurality of signal-generating processes, the noise-reduction goal value may be determined by using a maximum or a difference between a maximum and a minimum of signal values of data points within a noise-level determining region of the data set selected from the plurality of data sets obtained from the plurality of signal-generating processes.

Alternatively, the noise-reduction goal value may be set with a threshold value. For example, a threshold for target detection or a threshold for noise analysis may be used for the noise-reduction goal value. The threshold for target detection refers to a threshold value used for determining the presence or absence of the target analyte. The threshold for noise analysis refers to a threshold value used for determining a noise level of a data set.

The threshold for target detection may be a predetermined value. Specifically, the threshold for target detection may be predetermined by empirical knowledge based on experiments. Alternatively, the threshold for target detection may be obtained by a mathematical process for a data set. The starting point of a signal-increasing region (e.g., an amplification region) may be calculated mathematically to determine the threshold for target. For example, the threshold for target detection may be determined based on peaks of $1^{st}$ or $2^{nd}$ derivative curve for the data set.

The threshold for noise analysis refers to a threshold value used for determining a noise level of a data set. The threshold for noise analysis indicates a bound or limit of an allowable magnitude of noise signal in the data set for detecting the target analyte. The threshold for noise analysis may be determined by various approaches depending on signal interpreting methods and types of noise signals.

For example, when a signal of a reaction is increased with increase of the amount of a target analyte in a sample, a signal increase unrelated to the presence or absence of the target analyte may cause a critical problem. Therefore, the noise level may be determined based on a maximum signal value within the noise-level determining region of the data set, then the noise level of the data set may be reduced to less than the threshold for noise analysis as a noise-reduction goal value. In this case, the threshold for noise analysis may be a maximum noise threshold.

When the noise signal generated by a signal-generating means or an analytical system causes a critical problem, a maximum, a minimum or an average of signal value within the noise-level determining region may be determined as a noise-level of the data set with no regard to the signal interpreting method. Accordingly, the threshold for noise analysis may be a minimum noise threshold, a maximum noise threshold or an average noise threshold.

The maximum noise threshold may be most common type for the threshold for noise analysis. Particularly, when the maximum noise threshold is designated as a threshold for noise analysis, the threshold for noise analysis may be determined as a value lower than the threshold for target analyte. When a signal value higher than the threshold for target detection is generated in a background signal region of the data set, it means that the data set is likely to result in false positive result. When a signal value higher than the threshold for noise analysis is generated in a background region, it means that the noise level of the data set is likely to result in false positive result.

The term used herein "threshold" is intended to encompass both the threshold for target detection and the threshold for noise analysis.

According to an embodiment, the noise-reduction goal value may be set with a threshold for noise analysis or a threshold for target detection.

The noise-reduction ratio is provided by a value provided by signal values of data points within a noise-level determining region and a noise-reduction goal value.

The noise-reduction ratio refers to the rate of signal decrease in the data set determined by considering the noise-reduction goal. The noise-reduction ratio may be determined differently in each data set depending on noise level of each data set. An identical noise-reduction ratio is applied to a plurality of data points in a data set.

According to an embodiment, the noise-reduction goal value may be set with a threshold for noise analysis or a threshold for target detection. According to an embodiment, the noise-reduction ratio may be provided by defining a ratio of (i) a maximum value of the signal values of the data points within the noise-level determining region to (ii) the noise-reduction goal value. For instance, when a value of 200 as a threshold is designated as a noise-reduction goal value, and the maximum value of signal values within the noise-level determining region is a value of 400, the noise-reduction ratio may be determined as a value of 2.

According to an embodiment, the noise-reduction goal value may be a difference between maximum and minimum values within a noise-level determining region of a data set which is used for determining the noise-reduction goal value. The noise-reduction ratio may be provided by defining a ratio of (i) the difference between maximum and minimum values of the signal values of the data points within a noise-level determining region to (ii) the noise-reduction goal value. For instance, when the difference between maximum and minimum values as a noise-reduction goal value is a value of 50, and the difference between maximum and minimum values of signal values within noise-level determining region is a value of 80, the noise-reduction ratio may be determined as a value of 1.6.

According to an embodiment, the signal-generating process is a process amplifying the signal value, and the noise-level determining region is selected within a background region of the data set obtained from the signal-generating process. Specifically, the signal-generating process is a PCR or a real-time PCR, and the noise-level determining region may be selected within the background region before a signal amplification region of the PCR or the real-time PCR.

Step (b): Calibration of the Data Set (S130)

A calibrated data set having a reduced noise level is provided by calibrating the signal values of a plurality of data points in the data set with the noise-reduction ratio. The noise-reduction ratio may be applied to the data point in various ways.

According to an embodiment, for calibrating the data set, the noise-reduction ratio may be applied to all of the data points in the data set. When signal values of all data points in the data set are reduced by the same rate, the noise level of the data set may be reduced without change of signal value ratio between the data points in the data set.

Alternatively, the noise-reduction ratio may be applied to a portion of the data points in the data set. The portion of the data points may be an entire target signal-generating region (e.g., an amplification region) or its portion, an entire background region or its portion, or an entire noise-level determining region or its portion. Alternatively, the portion of the data points may be a portion of the data points throughout the three regions described above.

According to an embodiment, the noise-reduction ratio may be applied to at least the data points of the signal generating region (e.g. amplification region). In such case, data points of the noise-level determining region may be not used for subsequent analysis such determining the presence or absence of a target analyte.

According to an embodiment, the noise-reduction ratio may be applied to a plurality of the data points within the noise-level determining region, or a plurality of the data points within both the noise-level determining region and a following region (e.g., an amplification region).

Specifically, the noise-reduction ratio may be applied to a plurality of the data points within the background region or within both the background region and the amplification region of the data set.

The noise-reduction ratio may be applied to the data points in various approaches. According to an embodiment, the noise-reduction ratio may be applied to the signal values of a plurality of the data points in the data set with the following mathematical equation 1 such that the calibrated data set having a reduced noise level is provided;

$$\text{Calibrated signal value of the calibrated data set} = \text{signal value of the data set/noise-reduction ratio} \qquad \text{Equation 1}$$

The signal value of the data set in Equation 1 refers to a signal value of the data set before calibrating the data set. Therefore, the signal value of the data set in Equation 1 may be a value of signal actually measured at a cycle of a signal-generating process (e.g., actual value of fluorescence intensity measured in an amplification reaction) or their modifications. The modifications may include mathematically processed values of measured signal values. The modifications may be performed independently from the calibration by using the noise-reduction ratio. Examples of the mathematical processing may include addition or subtraction of a certain value.

The calibrated signal value of the calibrated data set in Equation 1 refers to a signal value of the data set calibrated by using the noise-reduction ratio. The calibrated data set may be provided by applying the Equation 1 to a signal value of the data set without additional processes. Alternatively, the calibrated data set may be provided by applying Equation 1 to a signal value of the data set and then performing an additional process. For example, the calibrated data set may be provided by applying Equation 1 to a signal value of the data set and then adding or subtracting a certain value to or from the signal value.

According to an embodiment, the calibrated data set having a reduced noise level may be used for qualitative or quantitative detection of the target analyte in the sample.

II. Method for Reducing Noise Level of a Data Set for Target Analyte with Additional Determination Step According to an embodiment, the method of present invention may further comprise the step of determining a need for the noise reduction before or after the step (a) of Section I.

A need for the noise reduction represents a need for reduction of a signal noise level of data points in a data set. The terms used herein "a need for the noise reduction" and "a need for reduction of the signal noise level" may be used interchangeably.

The need for the noise reduction may be determined (i) by evaluating a noise level of the data set of the target analyte in a sample and then comparing the noise level of the data set with the noise-reduction determinative value; or (ii) by considering the noise-reduction ratio.

When the need for the noise reduction for the calibrated data set is evaluated again after the calibration, the calibrated data set would be determined to have no need to reduce the noise level any more. Therefore, according to an embodiment, the noise-reduction goal value may be determined as a value to fulfill a requirement such that when the need of the noise reduction for the calibrated data set having undergone the calibration is evaluated once more after the calibration, the calibrated data set is determined to have no need to further reduce the noise level.

(1) Determination of the Need for the Noise Reduction Using a Noise-Reduction Determinative Value.

According to an embodiment, the need for the noise reduction may be determined by evaluating a noise-level of the data set of the target analyte in a sample and then comparing the noise-level of the data set with the noise-reduction determinative value.

According to an embodiment, the determination of the need for the noise reduction by comparing the noise-level of the data set with the noise-reduction determinative value may be performed before or after the step (a).

The term used herein "noise-reduction determinative value" refers to a reference value for determining the need for a noise reduction for a data set for a target analyte.

The noise-reduction determinative value may be reference values for determining the need for the noise reduction for the data set. The type or magnitude of the reference values for determining the need for the noise reduction may be different depending on signal-generating process, signal-generating means or target analyte.

For instance, the reference values for determining the need for the noise reduction for the data set may be designated with a certain signal value per se. In this case, the need for the noise reduction for the data set is determined by comparing a maximum or minimum signal value within a noise-level determining region of the data set to a certain signal value as a noise-reduction determinative value. Alternatively, the reference values for determining the need for the noise reduction for the data set may be calculated based on a measured signal values. For example, the need for the noise reduction for the data set may be determined based on a range of fluctuation, deviation or average of the measured signal values within a specific range. Alternatively, the reference values for determining the need for the noise reduction for the data set may be an incidence of a specific signal value. For example, the need for the noise reduction for the data set may be determined based on the occurrence frequency of signal values higher than a specific value.

The noise-reduction determinative value may be provided by various approaches.

The noise-reduction determinative value may be determined with consideration of a signal-generating process, signal-generating means, target analyte or analytical instrument. Alternatively, the noise-reduction determinative value may be determined by using an experimentally determined value.

Specifically, the noise-reduction determinative value may be provided by using a data set for providing a noise-reduction determinative value obtained by an experimental process.

The data set provided for determining the noise-reduction determinative value may be a data set obtained by a reference signal-generating process for determining the need for the noise reduction. Alternatively, when the signal-generating process is a plurality of signal-generating processes, the data set provided for determining the noise-reduction determinative value may be selected from a plurality of data sets obtained from the plurality of signal-generating processes.

According to an embodiment, the noise-reduction determinative value may be provided by using a signal value within a noise-level determining region of a control data set obtained from a signal-generating process which is a control signal-generating process for determining the need for the noise reduction.

The noise-reduction determinative value may be provided from a control data set. The control data set may be obtained from a control signal-generating process for determining the need for the noise reduction. The control signal-generating process is a standard and noise-free signal-generating process performed separately from the signal-generating process for determining the target analyte in the sample.

For example, the noise-reduction determinative value may be provided by using a signal value within a noise-level determining region of a data set obtained from a separated signal-generating process which is separated from a signal-generating process for the target analyte. According to an embodiment, the separated signal-generating process may be performed under the same conditions as the signal-generating process for the target analyte. This separated signal-generating process is named herein as "control signal-generating process". The control signal-generating process may be performed under the substantially same condition as the signal-generating process for the target analyte. The term "substantially same condition" may be exemplified by conditions under which the two signal-generating processes are performed using the same primers (and/or probes), labels, concentrations of reactants, reaction temperatures, detection temperatures, cycle number and type of instrument in different reaction vessels from each other.

According to an embodiment, the noise-reduction determinative value which is used for determining the need for the noise reduction may a value lower than a noise level of a data set for a target analyte in a sample.

Alternatively, according to an embodiment, when the signal-generating process is a plurality of signal-generating processes, the noise-reduction determinative value may be provided by using signal values within the noise-level determining region of at least one data set selected from a plurality of data sets obtained from a plurality of signal-generating processes.

The noise-reduction determinative value may be determined by using the data set for the target analyte without using the control signal-generating process. Specifically, when an identical target analyte is detected by each of data sets for a plurality of samples each of which is analyzed using the same signal-generating process, their noise levels may be determined by analyzing a plurality of data sets so that a noise-reduction determinative value may be provided.

Specifically, the noise-reduction determinative value may be provided by using signal values within a noise-determining region of a data set having a minimum noise level of a plurality of data sets obtained from a plurality of signal-generating processes. Otherwise, the noise-reduction determinative value may be provided by using signal values within a noise-determining region of a plurality of data sets obtained from a plurality of signal-generating processes. In this case, the noise-reduction determinative value may be provided by using a value obtained by a mathematical process of the signal value.

Meanwhile, the noise-reduction determinative value may be provided by using one of the signal values within a noise-level determining region of a data set provided for determining the noise-reduction determinative value. For example, the noise-reduction determinative value may be a maximum or minimum value of the signal values within the noise-determining region of the data set obtained from a control signal-generating process for determining the need for the noise reduction.

Otherwise, the noise-reduction determinative value may be provided by using mathematically processed signal values within the noise-level determining region of the data set provided for determining the noise-reduction determinative value. For example, the noise-reduction determinative value may be a difference between a maximum and a minimum, an average, a variance, a standard deviation or a coefficient of variation of the signal values within the noise-determining region of the data set obtained from a control signal-generating process for determining the need for the noise reduction.

When the noise-reduction determinative value is provided by using mathematically processed signal values, the noise level may be provided by using the same mathematical processing. For example, when the noise-reduction determinative value is a coefficient of variation of the signal value, the noise level of a data set may be provided by using a coefficient of variation.

According to an embodiment, the noise-reduction determinative value may be determined by using at least one characteristics of signal values of data points within a noise level determining region of the a data set obtained from the control signal-generating process for determining the noise-reduction determinative value selected from the group consisting of (i) a maximum; (ii) a difference between a maximum and a minimum; (iii) an average; (iv) a variance; (v) a standard deviation and (vi) coefficient of variation of signal values of data points within a noise level determining region of the a data set obtained from the control signal-generating process for determining the noise-reduction determinative value.

Specifically, the noise-reduction determinative value may be determined by using (i) a maximum; or (ii) a difference between a maximum and a minimum of signal values of data points within a noise level determining region of the a data set obtained from the control signal-generating process for determining the noise-reduction determinative value.

Alternatively, the noise-reduction determinative value may be a value less than signal values of the data points within the noise-level determining region in the data set obtained from the signal-generating process. In this case, the noise-reduction determinative value is determined in considering the purpose, sensitivity, specificity or condition of an analysis, or characteristics of analytical instruments.

According to an embodiment, when the signal-generating process is a plurality of signal-generating processes, the noise-reduction determinative value may be determined by using at least one characteristics of signal values of data points within a noise-level determining region of the data set selected from the plurality of data sets obtained from the plurality of signal-generating processes selected from the group consisting of (i) a maximum; (ii) a difference between a maximum and a minimum; (iii) an average; (iv) a variance; (v) a standard deviation and (vi) a coefficient of variation; of signal values of data points within a noise-level determining region of the data set selected from the plurality of data sets obtained from the plurality of signal-generating processes. Specifically, the noise-reduction determinative value may be determined by using (iii) an average or (vi) a coefficient of variation of signal values of data points within a noise-level determining region of the data set selected from the plurality of data sets obtained from the plurality of signal-generating processes.

According to an embodiment, when the signal-generating process is a plurality of signal-generating processes, the noise-reduction determinative value may be determined by using a maximum or a difference between a maximum and a minimum of signal values of data points within a noise-level determining region of the data set selected from the plurality of data sets obtained from the plurality of signal-generating processes.

Alternatively, the noise-reduction determinative value may be a threshold value. For example, a threshold for target detection or a threshold for noise analysis may be used for the noise-reduction determinative value. The threshold for target detection refers to a threshold value used for determining the presence or absence of the target analyte. The threshold for noise analysis refers to a threshold value used for determining a noise level of a data set.

When a signal of a reaction is increased with increase of the amount of a target analyte in a sample, a signal increase unrelated to the presence or absence of the target analyte may cause a critical problem. Therefore, the noise level may be determined based on a maximum signal value within the noise-level determining region of the data set, then the need for the noise reduction may be determined by comparing the noise level and the threshold for noise analysis as a noise-reduction determinative value. In this case, the threshold for noise analysis may be a maximum noise threshold.

When a signal of a reaction is decreased with increase of the amount of a target analyte in a sample, a signal decrease unrelated to the presence or absence of the target analyte may cause a critical problem. Therefore, the noise level may be determined based on a minimum signal value within the noise-level determining region of the data set, then the need for the noise reduction may be determined by comparing the noise level and the threshold for noise analysis as a noise-reduction determinative value. In this case, the threshold for noise analysis may be a minimum noise threshold.

According to an embodiment, the noise-reduction determinative value may be set with a threshold for noise analysis or a threshold for target detection Particularly, it is preferable that a data set for providing the noise-reduction goal value is identical to that for providing the noise-reduction determinative value.

According to an embodiment, the noise-reduction goal value may be determined by the noise-reduction determinative value. Specifically, the noise-reduction goal value may be a value identical to the noise-reduction determinative value. Otherwise, the noise-reduction goal value may be a value less than the noise-reduction determinative value. If the noise-reduction goal value is determined with a value less than the noise-reduction determinative value, the calibrated data set may be determined to have no need to further reduce the noise level upon calibrating the data set by using the noise-reduction goal value.

For example, when the noise-reduction determinative value is a maximum signal values within a noise-level determining region of a data set which is used for determining the noise-reduction determinative value, the noise-reduction goal value may be a value less than the maximum signal value. When the noise-reduction determinative value is a difference between maximum signal value and minimum signal value within a the noise-level determining region of a data set which is used for determining the noise-reduction determinative value, the noise-reduction goal value may be a value less than the difference between maximum signal value and minimum signal value.

According to an embodiment, the need for the noise reduction may be determined by comparing the noise level of the data set with the noise-reduction determinative value. Specifically, the need for the noise reduction may be determined by comparing magnitudes of the noise level of the data set with the noise-reduction determinative value.

For example, when the noise level is a maximum signal value within the noise-determining region of the data set and the noise-determinative value is a threshold for noise reduction, the data set may be determined to have the need to reduce the noise level with a proviso that the maximum signal value as the noise level is higher than the threshold as the noise-reduction determinative value.

The data set may be generally determined to have a need for reduction of the noise level when the noise level of a data set is higher than the noise-reduction determinative value. However, even when the noise level of a data set is less than the noise-reduction determinative value, the data set may be determined to have a need for reduction of the noise level depending on the signal interpreting method described above.

According to an embodiment, the need for the noise reduction may be determined by evaluating whether the noise level is not less than or less than the noise-reduction determinative value. Otherwise, the need for the noise reduction may be determined by evaluating whether the noise level is more than or not more than the noise-reduction determinative value.

When the noise level is equal to the noise-reduction determinative value, the result of the evaluation may be varied depending on the relationship between the noise-reduction determinative value and the noise-reduction goal value or depending on the type of the noise-reduction determinative value.

For example, when the noise-reduction determinative value is a threshold for target detection, the noise level equal to the noise-reduction determinative value may be determined as having a need to be reduced. Moreover, when the noise-reduction determinative value is equal to the noise-reduction goal value, the noise level equal to the noise-reduction determinative value is determined as having no need to be reduced.

The common descriptions between the noise-reduction determinative value and the noise-reduction goal value are omitted in order to avoid undue redundancy leading to the complexity of this specification.

(2) Determination of the Need for the Noise Reduction by Considering the Noise Reduction Ratio According to an embodiment, the need for the noise reduction may be determined by considering the noise-reduction ratio.

According to an embodiment, the determination of the need for the noise reduction by considering the noise reduction ratio may be performed after the step (a).

According to an embodiment, the need for the noise reduction may be determined by comparing the noise-reduction ratio with a predetermined value.

For example, if the determined noise-reduction ratio is more than a predetermined value, the data set is determined to have the need to reduce the noise level; otherwise, the data set is determined to have no need to reduce the noise level When the noise-reduction goal value is set with a threshold for target detection and the noise-reduction ratio is defined as a ratio of the noise level of the data set to the noise reduction goal value, the predetermined value may be equal to or less than 1 (e.g. 0.9, 0.8 or less). With this, when the predetermined value is equal to 1, a data set of which a noise level is equal to or more than the noise-reduction goal value may be selectively calibrated to reduce the noise level. Moreover, a data set of which a noise level is equal to or more than 90%, 80% or less of the noise-reduction goal value may be selectively calibrated to reduce the noise level by designating the predetermined value 0.9, 0.8 or less. The predetermined value used for determining the need for the noise reduction by being compared with the noise-reduction ratio may be equal to or less than 1, 0.99, 0.98, 0.97, 0.95, 0.94, 0.93, 0.92, 0.91, 0.9, 0.8, 0.7, 0.6, 0.5, 0.4, 0.3, 0.2 or 0.1.

For selectively calibrating the data set having a noise level which is statistically similar to the noise-reduction goal value, the predetermined value may be 0.9-0.95. For preventing the false positive result in determining more accurately a target analyte, the predetermined value may be in the range of 0.6-0.9.

According to an embodiment, when the need for the noise reduction is determined by comparing the noise-reduction ratio with a predetermined value, the noise-reduction ratio is applied to the signal values of a plurality of the data points in the data set in accordance with the following mathematical equation 2 such that the calibrated data set having a reduced noise level is provided;

$$\text{Calibrated signal value of the calibrated data set} = \text{signal value of the data set} \times \text{predetermined value/noise-reduction ratio} \qquad \text{Equation 2:}$$

wherein the predetermined value is used for determining the need for the noise reduction by being compared with the noise-reduction ratio.

Meanwhile, if the noise level of the calibrated data set calibrated by using the noise-reduction ratio is less than the noise level of the data set before calibration, the data set is determined to have the need to reduce the noise level.

By additionally performing the step of determining the need for the noise reduction, the data set is calibrated more selectively such that the noise level of the data set would be processed more efficiently.

III. Method for Analyzing the Target Analytes

Because the data set calibrated by the present method may give a quantitative or qualitative information for a target analyte, the present method is also described as "a method for detecting a target analyte in a sample" or "a method for analyzing a target analyte in a sample".

The term used herein "quantitative/qualitative analysis or detection" refers to analyzing or detecting a target analyte in a sample in a quantitative or qualitative manner using a data set obtained from a signal-generating process for the target analyte. The quantitative/qualitative analysis or detection may include analysis or detection of the presence or absence of the target analyte, the amount of the target analyte or a change of the amount by a biological or chemical reaction.

The terms used herein "a method for analyzing a target analyte in a sample" and "a method for detecting a target analyte in a sample" or "quantitative or qualitative analysis of a target analyte in a sample" and "quantitative or qualitative detection of a target analyte in a sample" are used to include obtaining information about the presence or absence of the target analyte, the amount of the target analyte or a change of the amount by a biological or chemical reaction and these terms may be used interchangeably.

In another aspect of this invention, there is provided a method for analyzing or detecting a target analyte in a sample, comprising:

(a) providing a noise-reduction ratio for reducing the noise level of the data set; wherein the data set is obtained from a signal-generating process for the target analyte using a signal-generating means; wherein the data set comprises a plurality of data points comprising cycles of the signal-generating process and signal values at the cycles; wherein the noise-reduction ratio is provided by a value provided by signal values of data points within a noise-level determining region and a noise-reduction goal value;

(b) providing a calibrated data set having a reduced noise level by calibrating the signal values of a plurality of data points in the data set with the noise reduction ratio.

(c) analyzing or detecting the target analyte in a sample quantitatively or qualitatively using the calibrated data set.

Since the method for detection described in Section III is a representative application of the method for reducing a noise level of a data set described in Section I, the common descriptions between them are omitted in order to avoid undue redundancy leading to the complexity of this specification.

According to the present method, the target analyte in a sample is analyzed or detected quantitatively or qualitatively using the calibrated data set.

According to an embodiment, the step of analyzing or detecting the target analyte quantitatively or qualitatively comprises the steps of: (i) determining in the data set a signal value corresponding to a predetermined threshold for target detection; (ii) determining a cycle of the signal value corresponding to the predetermined threshold; and (iii) analyzing or detecting the target analyte quantitatively or qualitatively using the determined cycle.

According to an embodiment, the method further comprises the step of determining the need for the noise reduction.

The need for the noise reduction may be determined (i) by evaluating a noise-level of the data set of the target analyte in a sample and then comparing the noise-level of the data set with the noise-reduction determinative value; or (ii) by considering the noise-reduction ratio.

According to an embodiment, the method further comprises the step of performing the signal-generating process to obtain a data set of the target analyte in the sample before the step (a).

In the present method for detecting or analyzing, the noise signal of the data set is reduced by using the reducing ratio and therefore the occurrence of false positive results may be reduced effectively with no risk of false negative results which may occur by unnecessary signal reduction.

IV. Storage Medium, Device and Computer Program

In another aspect of this invention, there is provided a computer readable storage medium containing instructions to configure a processor to perform a method for reducing a noise level of a data set for target analyte in a sample comprising:

(a) providing a noise-reduction ratio for reducing the noise level of the data set; wherein the data set is obtained from a signal-generating process for the target analyte using a signal-generating means; wherein the data set comprises a plurality of data points comprising cycles of the signal-generating process and signal values at the cycles; wherein the noise-reduction ratio is provided by a value provided by signal values of data points within a noise-level determining region and a noise-reduction goal value;

(b) providing a calibrated data set having a reduced noise level by calibrating the signal values of a plurality of data points in the data set with the noise reduction ratio.

In another aspect of this invention, there is provided a computer program to be stored on a computer readable storage medium to configure a processor to perform a method for reducing a noise level of a data set for target analyte in a sample comprising:

(a) providing a noise-reduction ratio for reducing the noise level of the data set; wherein the data set is obtained from a signal-generating process for the target analyte using a signal-generating means; wherein the data set comprises a plurality of data points comprising cycles of the signal-generating process and signal values at the cycles; wherein the noise-reduction ratio is provided by a value provided by signal values of data points within a noise-level determining region and a noise-reduction goal value;

(b) providing a calibrated data set having a reduced noise level by calibrating the signal values of a plurality of data points in the data set with the noise reduction ratio.

The program instructions are operative, when performed by the processor, to cause the processor to perform the present method described above. The program instructions for performing the method for reducing a noise level of a data set for target analyte in a sample may comprise an instruction to provide a noise-reduction ratio; and an instruction to provide a calibrated data set having a reduced noise level by calibrating the signal value of a plurality of data points in the data set with the noise reduction ratio.

The present method described above is implemented in a processor, such as a processor in a stand-alone computer, a network attached computer or a data acquisition device such as a real-time PCR machine.

The types of the computer readable storage medium include various storage medium such as CD-R, CD-ROM, DVD, flash memory, floppy disk, hard drive, portable HDD, USB, magnetic tape, MINIDISC, nonvolatile memory card, EEPROM, optical disk, optical storage medium, RAM, ROM, system memory and web server.

The data set may be received through several mechanisms. For example, the data set may be acquired by a processor resident in a PCR data acquiring device. The data set may be provided to the processor in a real time as the data set is being collected, or it may be stored in a memory unit or buffer and provided to the processor after the experiment has been completed. Similarly, the data set may be provided to a separate system such as a desktop computer system via a network connection (e.g., LAN, VPN, intranet and Internet) or direct connection (e.g., USB or other direct wired or wireless connection) to the acquiring device, or provided on a portable medium such as a CD, DVD, floppy disk, portable HDD or the like to a stand-alone computer system. Similarly, the data set may be provided to a server system via a network connection (e.g., LAN, VPN, intranet, Internet and wireless communication network) to a client such as a notebook or a desktop computer system.

The instructions to configure the processor to perform the present invention may be included in a logic system. The instructions may be downloaded and stored in a memory module (e.g., hard drive or other memory such as a local or attached RAM or ROM), although the instructions can be provided on any software storage medium such as a portable HDD, USB, floppy disk, CD and DVD. A computer code for implementing the present invention may be implemented in a variety of coding languages such as C, C++, Java, Visual Basic, VBScript, JavaScript, Perl and XML. In addition, a variety of languages and protocols may be used in external and internal storage and transmission of data and commands according to the present invention.

In still further aspect of this invention, there is provided a device for reducing a noise level of a data set for a target analyte in a sample, comprising (a) a computer processor and (b) the computer readable storage medium described above coupled to the computer processor.

According to an embodiment, the device further comprises a reaction vessel to accommodate the sample and signal-generating means, a temperature controlling means to control temperatures of the reaction vessel and/or a detector to detect signals at amplification cycles.

The processor may be prepared in such a manner that a single processor can do all performances described above. Alternatively, the processor unit may be prepared in such a manner that multiple processors do multiple performances, respectively.

According to an embodiment, the processor may be embodied by installing software into conventional devices for detection of target nucleic acid molecules (e.g. real-time PCR device).

According to an embodiment, a calibrated data set is provided in such a manner that data set of a target analyte is obtained and a noise-reduction ratio is provided by a value provided by signal values of data points within a noise-level determining region and a noise-reduction goal value.

A noise-level determining region and a noise-reduction goal value may be arbitrarily determined by users or system suppliers. Alternatively, the noise-level determining region and the noise-reduction goal value may be determined by a device of the present invention. For example, the device of the present invention which collects a plurality of data sets may be capable of determining a noise-level determining region and the noise-reduction goal value with consideration of signal values of the plurality of data sets.

In still further aspect of this invention, there is provided a computer readable storage medium containing instructions to configure a processor to perform a method for detecting or analyzing a target analyte in a sample by reducing a noise level of the data set for the target analyte.

In still further aspect of this invention, there is provided a computer program to be stored on a computer readable storage medium to configure a processor to perform a method for detecting or analyzing a target analyte in a sample by reducing a noise level of the data set for the target analyte.

In still further aspect of this invention, there is provided a device for detecting or analyzing a target analyte in a sample by reducing a noise level of the data set for the target analyte, comprising (a) a computer processor and (b) the computer readable storage medium described above coupled to the computer processor.

The storage medium, device and computer program described in Section IV is an application of the method in Section I implemented by computer, the common descriptions between them are omitted in order to avoid undue redundancy leading to the complexity of this specification.

The feature and advantages of this invention will be summarized as follows:

(a) The present invention can reduce a noise level of a data set to a suitable level in more efficient and convenient manner by applying a noise-reduction ratio to the data set, thereby reducing effectively the occurrence of false positive results may be reduced.

(b) According to the present invention, the calibrated data set is obtained by using the noise-reduction ratio such that the noise level of a data set is reduced without change of signal ratio between the data points in the data set.

(c) The present invention can reduce the noise level of a data set by applying a noise-reduction ratio to the data set such that the calibrated data set may be obtained more practically and more reliably than conventional technologies which use subtraction of a specific value from the data set for reducing a noise level.

(d) Generally, it has been known to one of skill in the art that a noise signal may be easily found in a background region but not in an amplification region because the signal of the amplification region is mostly composed of a signal originated from a target analyte.

In conventional technologies, a cycle having an abnormal signal is detected and then its signal value is corrected. Therefore, the conventional technologies have a limitation in detecting and calibrating a noise signal in the amplification region. However, in the present method, the entire signal values of the data set may be calibrated based on a noise level of a selected specific region, whereby a noise level in an amplification region may be also calibrated easily.

(e) Depending on the noise level of the data set, both the need for executing a noise reduction process and a level of noise reduction may be determined and therefore a fine calibration of the data set becomes practicable depending on the noise level.

(f) Furthermore, the present method has advantages in which a data calibration is performed after determining whether the reduction of a signal noise is necessary or not, thus excluding the unnecessary data calibration.

(g) The present method makes it possible to adjust the range and level of the data calibration because the noise-reduction determinative value can be established differently from the noise-reduction goal value.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Acquisition of Amplification Curves and Identification of Determination Error of Target Nucleic Acid In the present invention, a method of reducing the signal noise level is used to remove an error in the results of detecting or quantifying a target nucleic acid in which the error is generated by the background noise signal. The data sets and amplification curves were obtained for the selected positive sample including a target nucleic acid and the selected negative samples 1, 2, and 3 by performing a real-time polymerase chain reaction (RT-PCR). The detection and quantification of the target nucleic acid were judged by using the amplification curves and the predetermined threshold for target detection. It was investigated whether a determination error in detecting and quantifying the target nucleic acid were generated.

<1-1> Acquisition of Amplification Profile Curves

The real-time polymerase chain reactions (RT-PCRs) were performed for the selected positive sample including a target nucleic acid and the selected negative samples 1, 2, and 3 by using a TaqMan probe as a signal-generating means on the CFX96™ Real-Time PCR Detection System (Bio-Rad Laboratories) with 45 amplification cycles. The original data sets including values of RFU (Relative Fluorescence Unit) for the respective cycles were obtained. The 'No Baseline Subtracted Amplification Curves' were prepared by plotting the obtained original data sets (x-axis: cycle and y-axis: RFU).

The baseline was established from the original data sets and 'No Baseline Subtracted Amplification Curves' by using the software of the CFX96™ Real-Time PCR Detection System (Bio-Rad Laboratories), and the 'Baseline Subtracted Amplification Curves' and their data sets were prepared by subtracting the calculated baseline.

The detection and quantification of the target nucleic acid were determined by using the 'Baseline Subtracted Amplification Curves' and their data sets. The sample showing a fluorescence value over a threshold for target detection after third cycle in the baseline subtracted amplification curve was determined as a positive, and the sample exhibiting a fluorescence value below a threshold for target detection after third cycle in the baseline subtracted amplification curves was determined as a negative. In this Example, the threshold for target detection was designated as the value of RFU 100.

The cycle number at the first crossing point ($1^{st}$ CP) between the line of the threshold for target detection and the amplification curve was designated as a threshold cycle (Ct) and the resulting Ct value was used for quantifying the target nucleic acid.

<1-2> False Positive Error in Detecting and Quantifying the Target Nucleic Acid

As shown in FIG. 2, among the negative samples 1, 2 and 3 not containing the target nucleic acid, the negative sample 1 was correctly determined as a negative, however the other negative samples 2 and 3 were incorrectly determined as a positive, which reveals that there were false positive errors in the detection method. Further, the positive sample containing the target nucleic acid also had an error in determining the Ct value representing the amount of an amplified product. The errors discussed above were caused by the background noise signal. This implies the fact that during the process of determining the results of detecting and quantifying the target nucleic acid in the sample with the predetermined threshold for target detection, a determination error can be generated due to the background noise signal variation which arises from the differences of the reaction conditions, environments or the instrument for the respective real time-polymerase chain reactions (RT-PCRs).

Example 2: Correction of Determination Error in Detecting Target Nucleic Acid by Using Signal Noise-Level Reduction Method with Noise-Reduction Goal Value In this Example, the background noise level was measured for the respective real-time PCRs and the noise level was calibrated to a desired level for the correction of the error in determining the results of detecting and quantifying the target nucleic acid. As shown in FIG. 1, this method was performed according to the following steps of (i) designation of the noise-level determining region and determination of the noise level (S110), (ii) determination of the noise-reduction ratio (S120), and (iii) calibration of the data set (S130). The calibration method in this example was carried out for the negative sample 3 and the positive sample of Example 1 in two different ways depending on the application modes of the noise-reduction goal value.

<2-1> Calibration of Data Using Noise Signal Variation

Figure 3A:
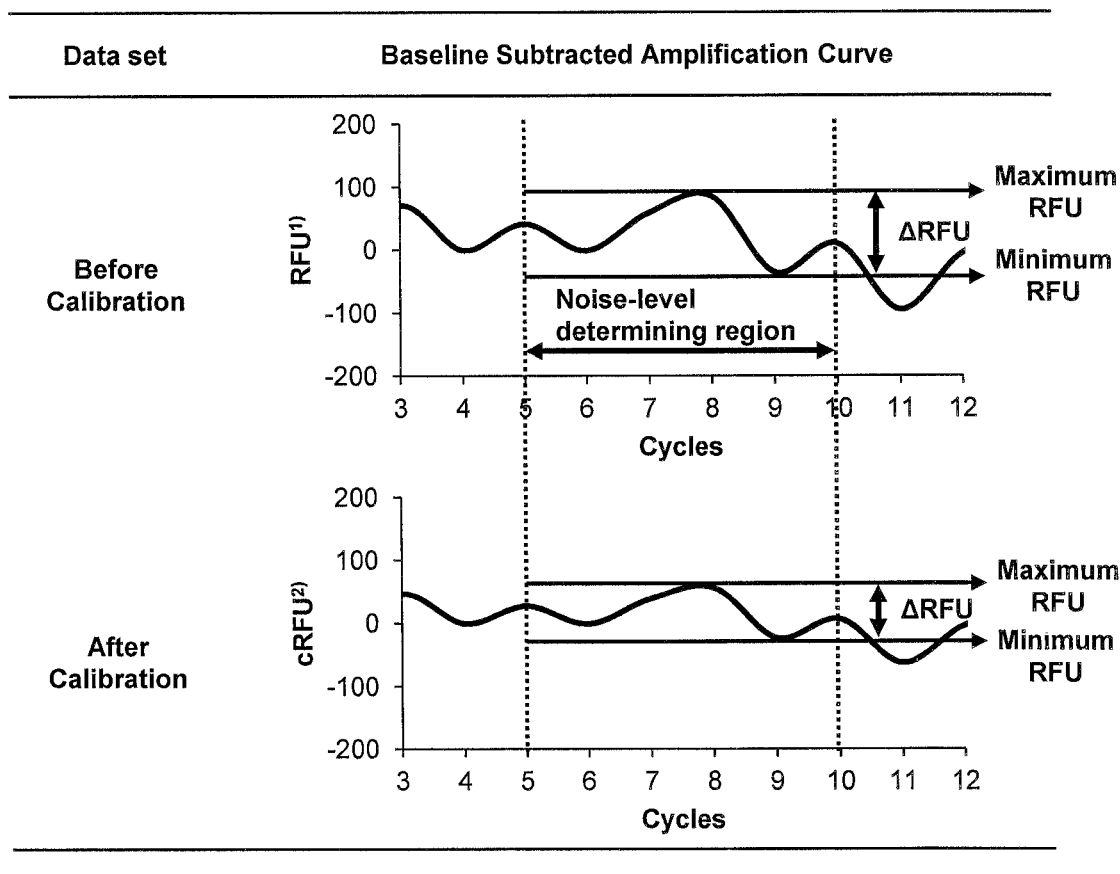
FIG. 3a represents the change of the noise level within the noise-level determining region of the data set by calibrating the data set using a difference between the maximum and the minimum signal values (ΔRFU) within the noise-level determining region.

As shown in FIG. 3A, in the calibration method of this Example, a specific background region was designated as a noise-level determining region in the baseline subtracted amplification curve and the data set was calibrated such that the noise signal variation (ΔRFU) in the noise-level determining region became the predetermined noise-reduction goal value.

<Step 1> Designation of Noise Level Determining Region and Determination of Noise Level of Sample The region of cycles 5-10 corresponding to a portion of a background region was designated as a noise-level determining region. The noise level of the sample was determined by a noise variation (ΔRFU) within the noise-level determining region in the data set obtained from the respective samples. The 'ΔRFU' was determined as follows:

Noise level of the sample (ΔRFU)=maximum RFU within the noise-level determining region−minimum RFU within the noise-level determining region The noise levels of the negative sample 3 and the positive sample were determined as ΔRFU 121 and ΔRFU 161, respectively.

<Step 2> Determination of Noise-Reduction Ratio and Calibration of Data

The noise-reduction ratio (N-ratio) was calculated from the noise level (ΔRFU) of the sample determined in the step 1 and the noise-reduction goal value designated as below. Afterwards, the signal values (RFUs) of the respective cycles were calibrated by using the calculated noise-reduction ratio (N-ratio).

Noise-reduction goal value=ΔRFU 80

Noise-reduction ratio (N-Ratio)=noise level (ΔRFU) of the sample÷Noise-reduction goal value Calibrated RFU (cRFU) of the respective cycle=RFU of the respective cycle÷N-ratio The calibrated data sets for the negative sample 3 and the positive sample were obtained according to the above method. The noise levels of the calibrated data sets were determined once again according to the steps 1 and 2. As a result, as shown in Table 1, it was verified that the noise levels of the calibrated data sets in the negative sample 3 and the positive sample had been reduced to the noise-reduction goal value of ΔRFU 80.

TABLE 1

| Sample | Data Set | Max-RFU[1] | Min-RFU[2] | ΔRFU | N-GV[3] | N-Ratio[4] |
|---|---|---|---|---|---|---|
| Negative Sample 3 | Before-Cali[5] | 86 | −35 | 121 | 80 | 1.51 |
|  | After-Cali[6] | 57 | −23 | 80 |  | 1.00 |
| Positive Sample | Before-Cali | 120 | −41 | 161 |  | 2.02 |
|  | After-Cali | 60 | −20 | 80 |  | 1.00 |

Max-RFU[1]: Maximum RFU;
Min-RFU[2]: Minimum RFU;
N-GV[3]: Noise-Reduction Goal Value;
N-Ratio[4]: Noise-Reduction Ratio;
Before-Cali[5]: Before Calibration;
After-Cali[6]: After Calibration.

The results of determining the presence of the target nucleic acid and measuring Ct value for the negative sample 3 and the positive sample were compared between before and after calibration.

Figure 3B:
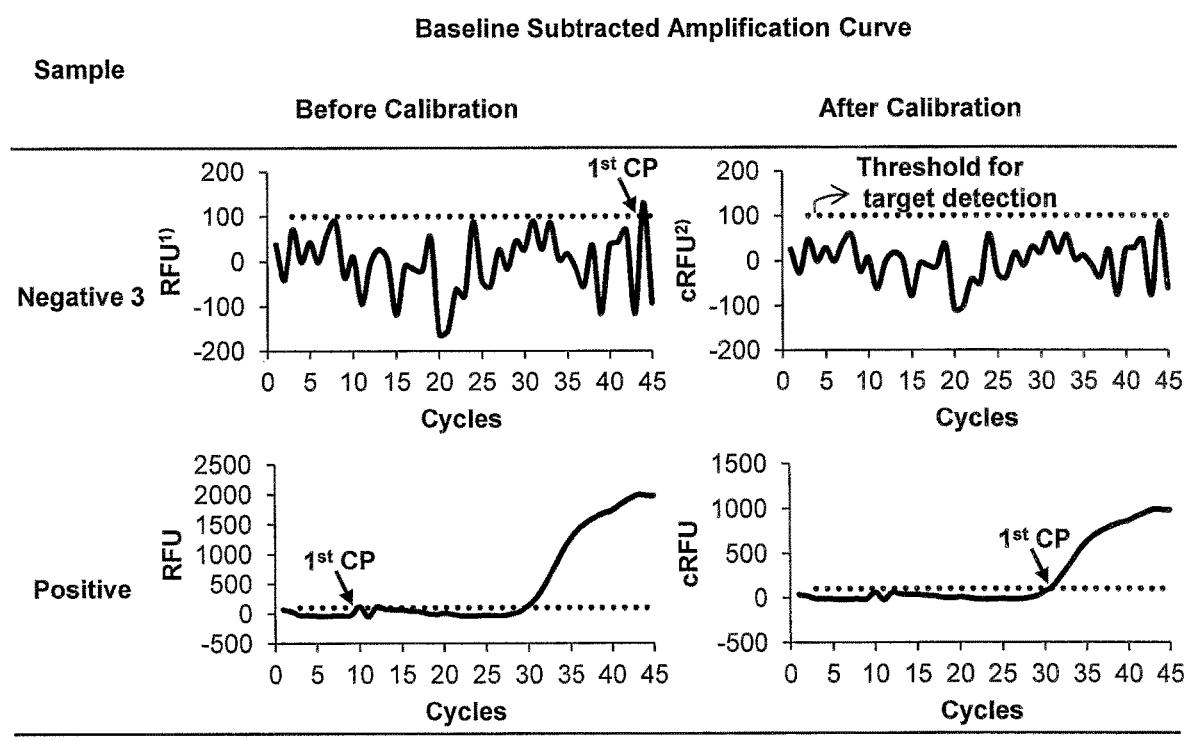
FIG. 3b represents the analysis results of a target nucleic acid molecule before and after the calibration of the data set using a difference between the maximum and the minimum signal values (ΔRFU) within the noise-level determining region.

As shown in FIG. 3B and Table 2, after calibration, the false positive error in the negative sample 3 was corrected and the Ct value determination error in the positive sample was also calibrated to the correct Ct value. These results demonstrated that the result determination error caused by the abnormal background noise signal would be removed by the data calibration which reduced the level of the background noise signal to the level of the noise-reduction goal value.

TABLE 2

| Sample | Threshold for Target Detection | Before Calibration | | After Calibration | |
|---|---|---|---|---|---|
| | | Ct value | Determination Result | Ct value | Determination Result |
| Negative Sample 3 | 100 | 43.88 | False Positive | — | Negative |
| Positive Sample | | 9.86 | Positive Ct value Error | 30.45 | Positive Correct Ct value |

<2-2> Calibration of Data Using Maximum Noise Signal

Figure 4A:
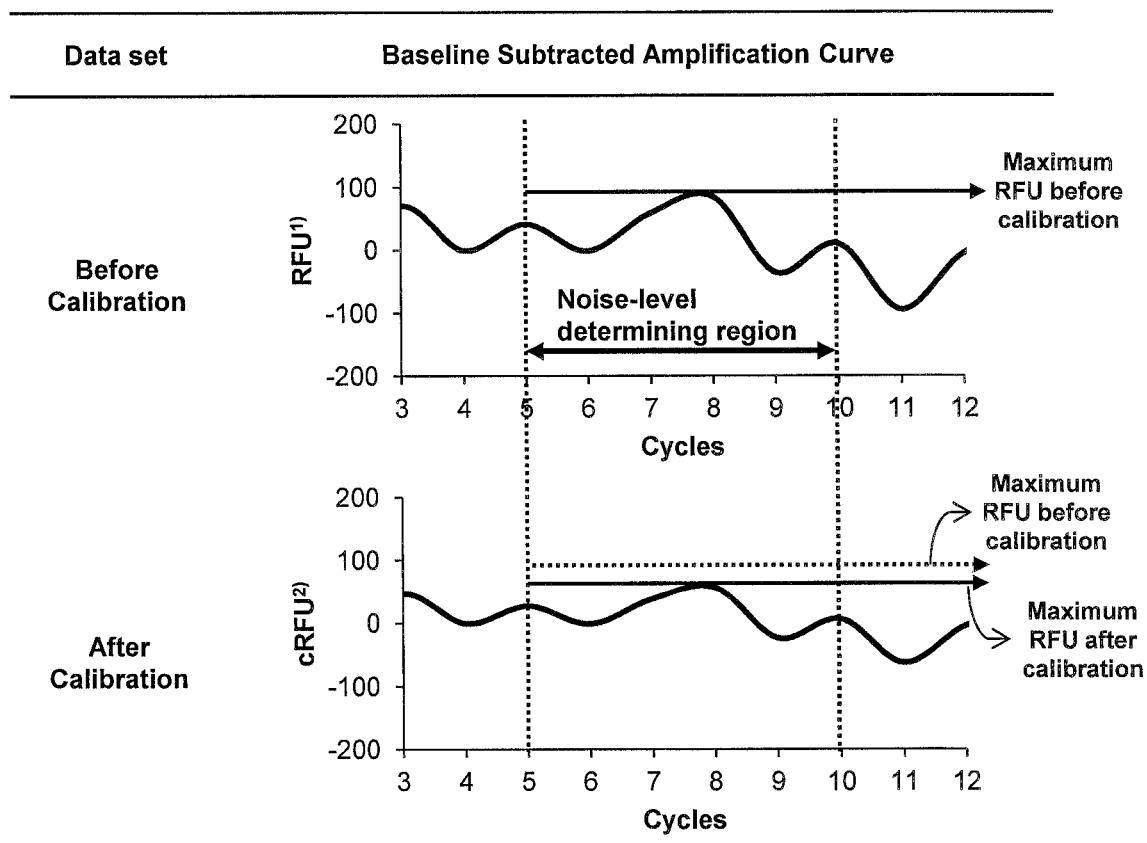
FIG. 4a represents the change of the noise level within the noise-level determining region of the data set by calibrating the data set using the maximum signal value (Maximum RFU) within the noise-level determining region.

As shown in FIG. 4A, in the calibration method of this Example, a specific background region was designated as a noise-level determining region in the baseline subtracted amplification curve and the data set underwent the calibration by using the maximum noise signal (Maximum RFU) in the noise-level determining region and the predetermined noise-reduction goal value.

<Step 1> Designation of Noise-Level Determining Region and Determination of Noise Level The region of cycles 5-10 corresponding to a portion of the background region was designated as a noise-level determining region. The noise level of the sample was determined by a maximum signal value (Maximum RFU) within the noise-determining region in the data set obtained from the respective samples. Specifically, the noise levels of the negative sample 3 and the positive sample were determined as Maximum ΔRFU 86 and Maximum ΔRFU 120 respectively.

<Step 2> Determination of Noise-Reduction Ratio and Calibration of Data Set

The noise-reduction ratio (N-ratio) was calculated from the noise level of the sample (Maximum RFU) determined in the step 1 and the noise-reduction goal value designated as below. The calibrations of signal values (RFUs) of the respective cycles were performed using the calculated noise-reduction ratio (N-ratio).

Noise-reduction goal value=Maximum RFU 60

Noise-reduction ratio(N-Ratio)=Maximum RFU÷Noise-reduction goal value

Calibrated RFU (cRFU) of the respective cycle=RFU of the respective cycle÷N-Ratio The calibrated data sets for the negative sample 3 and the positive sample were obtained according to the above-described method. The noise-reduction goal value can be designated as any value below the predetermined threshold for target detection. In this Example, the noise-reduction goal value was designated as the value corresponding to 60% of the threshold for target detection (RFU 100).

The noise levels of the calibrated data sets were determined once again according to the steps 1 and 2. As a result, as shown in Table 3, it was verified that the noise levels of the calibrated data sets in the negative sample 3 and positive sample had been reduced to the noise-reduction goal value of Maximum RFU 60.

TABLE 3

| Sample | Data Set | Maximum RFU | N-GV[1] | N-Ratio[2] |
|---|---|---|---|---|
| Negative Sample 3 | Before Calibration | 86 | 60 | 1.43 |
| | After Calibration | 60 | | 1.00 |
| Positive Sample | Before Calibration | 120 | | 2.00 |
| | After Calibration | 60 | | 1.00 |

N-GV[1]: Noise-Reduction Goal Value;
N-Ratio[2]: Noise-Reduction Ratio.

Figure 4B:
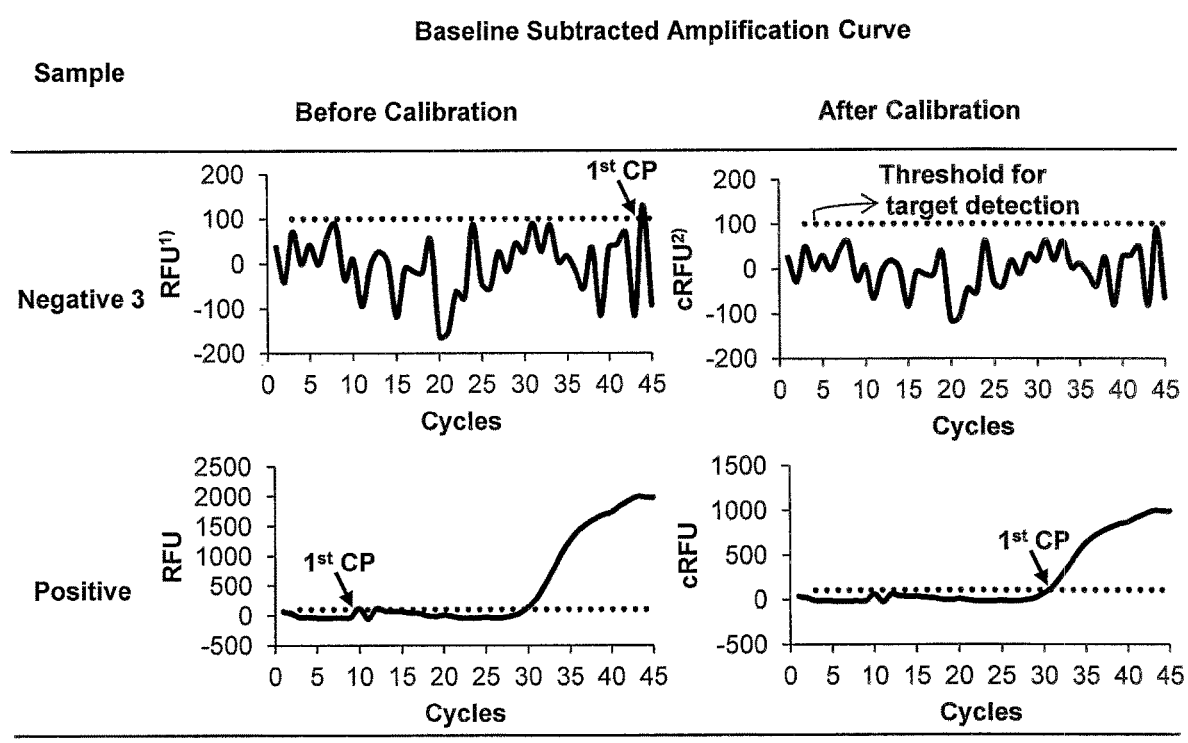
FIG. 4b represents the analysis results of a target nucleic acid molecule before and after the calibration of the data set using the maximum signal value (Maximum RFU) within the noise-level determining region.

The results of determining the presence of the target nucleic acid and measuring Ct value for the negative sample 3 and positive sample were compared between before and after calibration. As shown in FIG. 4B and Table 4, after calibration, the false positive error in the negative sample 3 had been corrected and the Ct value determination error in the positive sample had been also calibrated to the correct Ct value. These results demonstrated that the result determination error caused by the abnormally strong background noise signal would be removed by the data calibration which reduced the noise level such that the maximum background noise signal remained below the threshold for target detection.

TABLE 4

| Sample | Threshold for Target Detection | Before Calibration | | After Calibration | |
|---|---|---|---|---|---|
| | | Ct value | Determination Result | Ct value | Determination Result |
| Negative Sample 3 | 100 | 43.88 | False Positive | — | Negative |
| Positive Sample | | 9.86 | Positive Ct value Error | 30.44 | Positive Correct Ct value |

The above results demonstrate that the method of the present invention is able to remove the errors in determining the presence or absence of the target nucleic acid, which are caused by the background noise signal, and is also able to precisely quantify the amplified product of the target nucleic acid.

Figure 5:
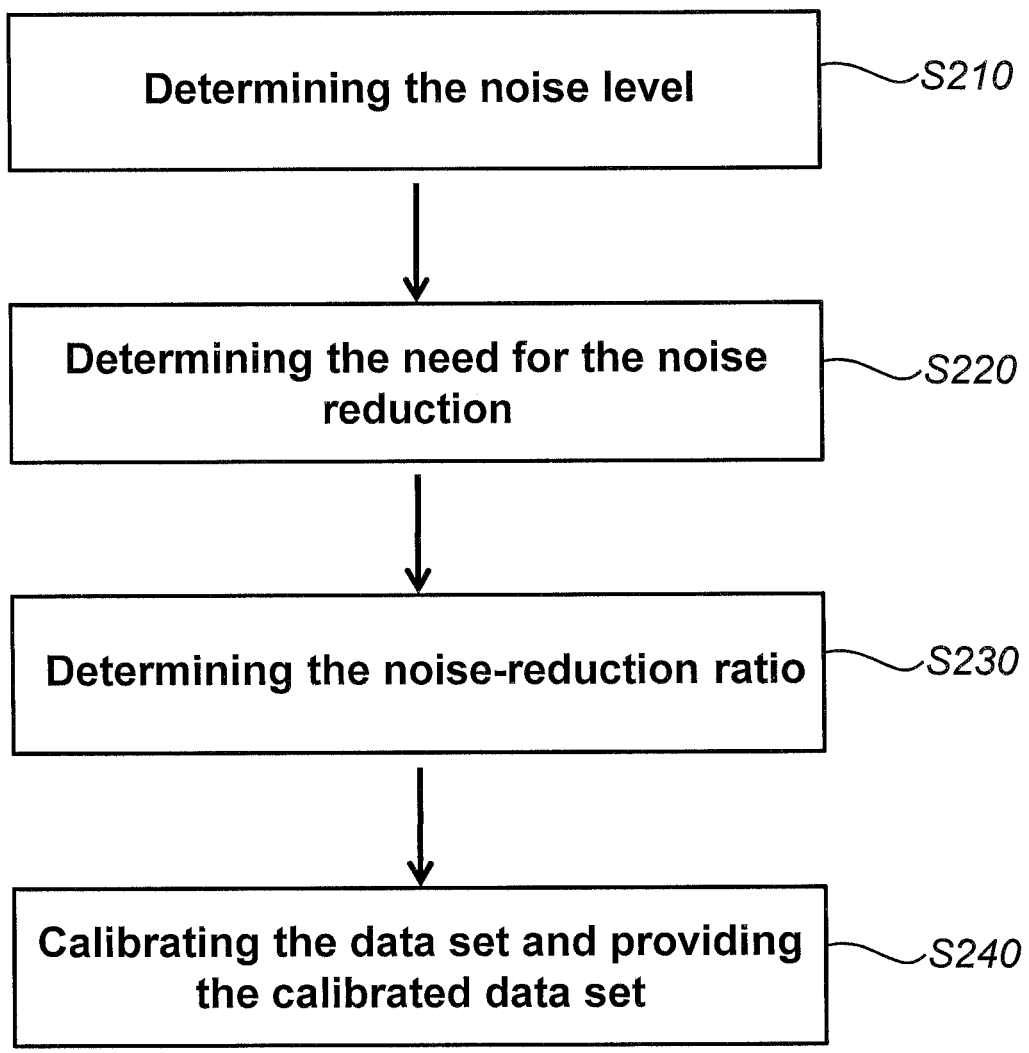
FIG. 5 represents a flow diagram illustrating an embodiment of the present method for reducing a noise level of a data set for a target analyte in a sample, in which the method further comprises the step of determining the need for the noise reduction.

Example 3: Correction of Determination Error in Detecting Target Nucleic Acid by Using Signal Noise-Level Reduction Method with Noise-Reduction Determinative Value and Noise-Reduction Goal Value The method in this example further comprises the step of determining the need for reduction of the background signal noise level. Thus, when the reduction of the signal noise level is determined to be necessary, the data set undergoes the calibration to correct the result determination error in the detection and quantification of the target nucleic acid. As shown in FIG. 5, this method was performed according to the following steps of (i) designation of the noise-level determining region and determination of the noise level (S210), (ii) determination of the need for reduction of the signal noise level (S220), (iii) determination of the noise-reduction ratio (S230), and (iv) calibration of the data (S240). The calibration method in this example was carried out in two different ways depending on the noise-reduction determinative value and the application modes of the noise-reduction goal value.

<3-1> Calibration of Data Using Noise Signal Variation

Figure 6A:
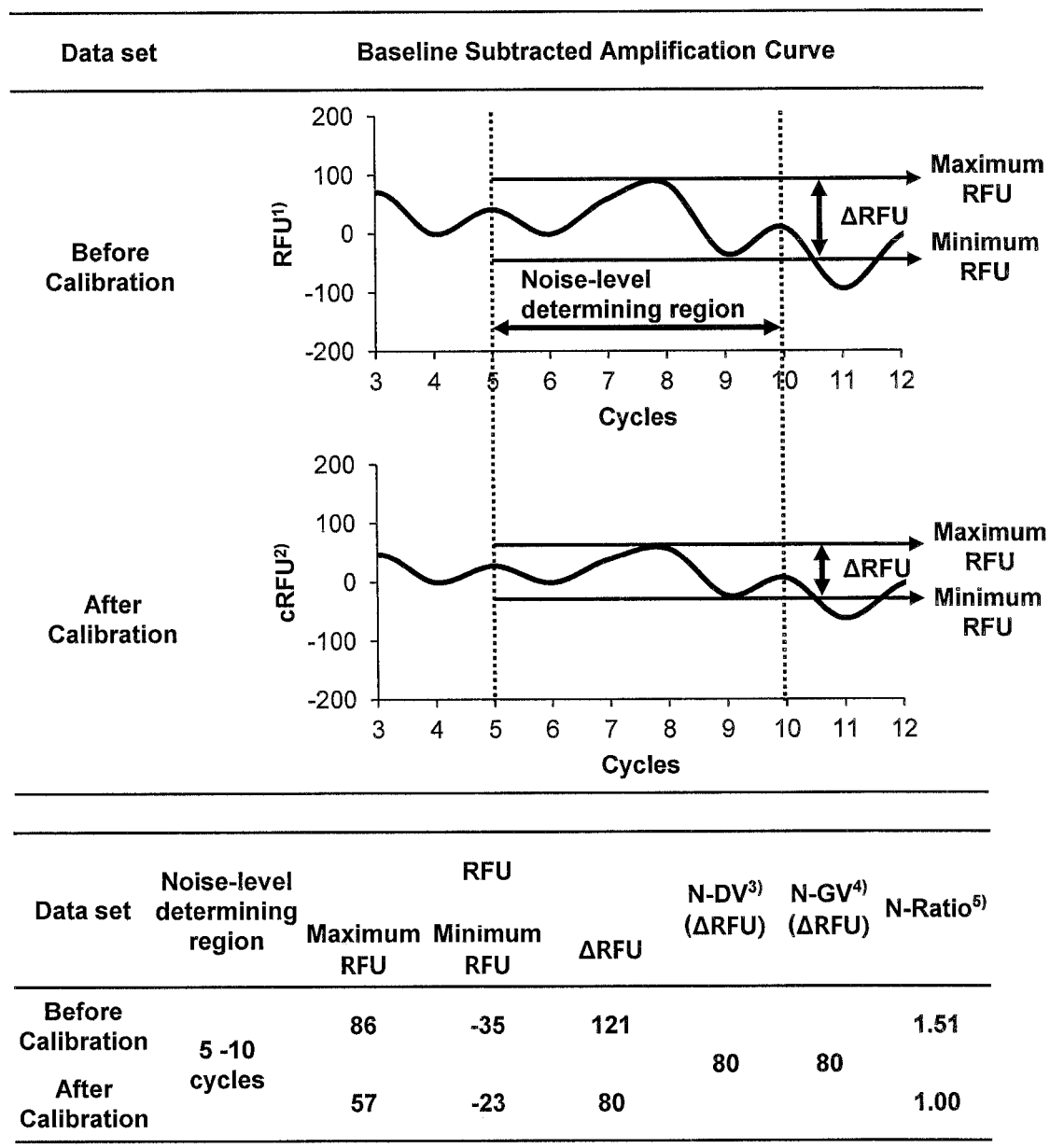
FIG. 6a represents the change of the noise level within the noise-level determining region of the data set by evaluating the need for the noise reduction and calibrating the data set using a difference between the maximum and the minimum signal values (ΔRFU) within the noise-level determining region, wherein the noise-reduction determinative value and the noise-reduction goal value are identical.
Figure 6B:
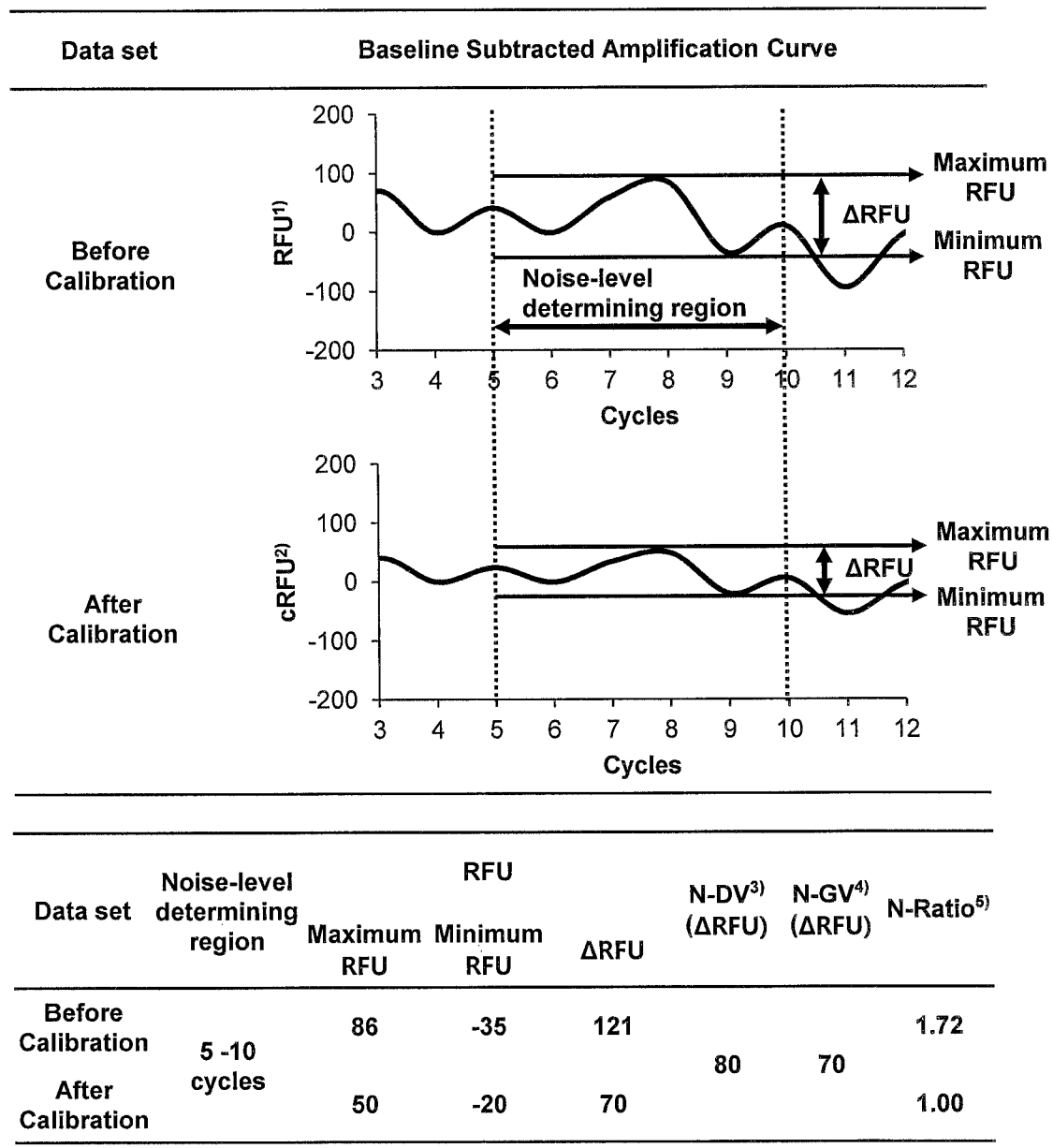
FIG. 6b represents the change of the noise level within the noise-level determining region of the data set by evaluating the need for the noise reduction and calibrating the data set using a difference between the maximum and the minimum signal values (ΔRFU) within the noise-level determining region, wherein the noise-reduction goal value is less than the noise-reduction determinative value.

As shown in FIGS. 6A-6B, a specific background region was designated as a noise level determining region in the baseline subtracted amplification curve. After comparing the noise signal variation (ΔRFU) in the noise level determining region with the determined noise-reduction determinative value, when the noise signal variation was equal to or below the noise-reduction determinative value, the data set did not undergo the calibration, whereas when the noise signal was over the noise-reduction determinative value, the data set underwent the calibration.

<Step 1> Designation of Noise-Level Determining Region and Determination of Noise Level of Sample The region of cycles 5-10 was designated as a noise-level determining region as same in Example <2-1>. As a result of determining the noise level of the respective samples, it was found that the noise levels of the negative samples 1, 2, and 3 and the positive sample were ΔRFU 68, ΔRFU 207, ΔRFU 121 and ΔRFU 161, respectively.

<Step 2> Determination of Need for Reduction of Signal Noise Level

The noise-reduction determinative value for evaluating the need for reduction of the signal noise level was determined as following in consideration of ΔRFU of the data set obtained through the separate control signal-generating process performed under the substantially same conditions as those of the signal-generating process of the present example.

Noise-reduction determinative value=ΔRFU 80

The need for reduction of the signal noise level of the data set was determined by comparing the noise level (ΔRFU) of the sample determined in the step 1 with the noise-reduction determinative value determined above. The decision criteria are described below.

Need for reduction of the signal noise level(application of the data calibration):noise level(ΔRFU) of the sample>noise-reduction determinative value No need for reduction of the signal noise level(no application of the data calibration):noise level (ΔRFU) of the sample≤noise-reduction determinative value Specifically, the need for reduction of the signal noise level was determined for the samples by using the background signal variation. As a result, as shown in Table 5, the noise signal variation in the noise level determining region of the negative sample 1 was calculated as ΔRFU 68, which was below ΔRFU 80 (i.e., noise reduction determinative value) and thus there is no need to reduce its noise level. On the other hand, the noise signal variations of the negative samples 2, 3, and the positive sample were calculated respectively as ΔRFU 207, ΔRFU 121 and ΔRFU 161, which were over ΔRFU 80 (i.e., noise-reduction determinative value) and thus there is a need to reduce their noise levels.

<Step 3> Determination of Noise-Reduction Ratio and Calibration of Data Set

The noise-reduction ratios (N-Ratios) were calculated using the noise-reduction goal value and the data sets of the negative samples 2 and 3 and the positive sample which had been determined as having a need for reduction of the noise level, and then the signal values (RFUs) of the respective cycles were calibrated according to the calculated noise-reduction ratio (N-Ratio).

The noise-reduction goal values could be designated in two different manners: (i) the same value as the noise-reduction determinative value; and (ii) the different value from the noise-reduction determinative value.

Noise-reduction goal value 1=ΔRFU 80

Noise-reduction goal value 2=ΔRFU 70

The noise-reduction ratio (N-Ratio) was calculated as below:

Noise-reduction ratio=noise level(ΔRFU) of the sample÷noise-reduction goal value As shown in Table 5, when the noise-reduction goal value 1 was used for the calculation of the noise-reduction ratio (N-Ratio), the N-Ratios of the negative samples 2 and 3 and the positive sample were determined as 2.59, 1.51 and 2.02 respectively. Further, when the noise-reduction goal value 2 was used for the calculation of the noise-reduction ratio (N-Ratio), the N-Ratios of the negative samples 2 and 3 and the positive sample were determined as 2.96, 1.72 and 2.30 respectively. The signal values of the respective cycles of the data sets were calibrated using the respective determined N-Ratios. The calibrated signal values of the respective cycles of the data sets were calculated as below:

Calibrated RFUs of the respective cycles=RFUs of the respective cycles÷N-Ratio

The calibrated data sets of the negative samples 2 and 3 and the positive sample were obtained according to the above method.

The noise levels for the obtained calibrated data sets were determined once again through the steps 1-3. As a result, as shown in Table 5, the noise levels of the calibrated data sets of the negative samples 2, 3 and the positive sample had been reduced to the noise-reduction goal value of ΔRFU 80 or ΔRFU 70. Accordingly, when the noise levels of the calibrated data sets were compared with the noise-reduction determinative value once more, it was found that there was no need for reduction of their noise levels any more.

TABLE 5

| Sample | Data Set | Max-RFU[1] | Min-RFU[2] | ΔRFU | N-DV[3] | N-GV[4] | N-Ratio[5] |
|---|---|---|---|---|---|---|---|
| Negative Sample 1 | Before-Cali[6] | 33 | −35 | 68 | 80 | 80 | — |
| | After-Cali[7] | — | — | — | | | — |
| Negative Sample 2 | Before-Cali | 158 | −49 | 207 | | | 2.59 |
| | After-Cali | 61 | −19 | 80 | | | 1.00 |
| Negative Sample 3 | Before-Cali | 86 | −35 | 121 | | | 1.51 |
| | After-Cali | 57 | −23 | 80 | | | 1.00 |
| Positive Sample | Before-Cali | 120 | −41 | 161 | | | 2.02 |
| | After-Cali | 60 | −20 | 80 | | | 1.00 |
| Negative Sample 1 | Before-Cali | 33 | −35 | 68 | | 70 | — |
| | After-Cali | — | — | — | | | — |
| Negative Sample 2 | Before-Cali | 158 | −49 | 207 | | | 2.96 |
| | After-Cali | 53 | −17 | 70 | | | 1.00 |
| Negative Sample 3 | Before-Cali | 86 | −35 | 121 | | | 1.72 |
| | After-Cali | 50 | −20 | 70 | | | 1.00 |
| Positive Sample | Before-Cali | 120 | −41 | 161 | | | 2.30 |
| | After-Cali | 52 | −18 | 70 | | | 1.00 |

Max-RFU[1]: Maximum RFU;
Min-RFU[2]: Minimum RFU;
N-DV[3]: Noise-Reduction Determinative Value;
N-GV[4]: Noise-Reduction Goal Value;
N-Ratio[5]: Noise-Reduction Ratio;
Before-Cali[6]: Before Calibration;
After-Cali[7]: After Calibration.

Figure 6C:
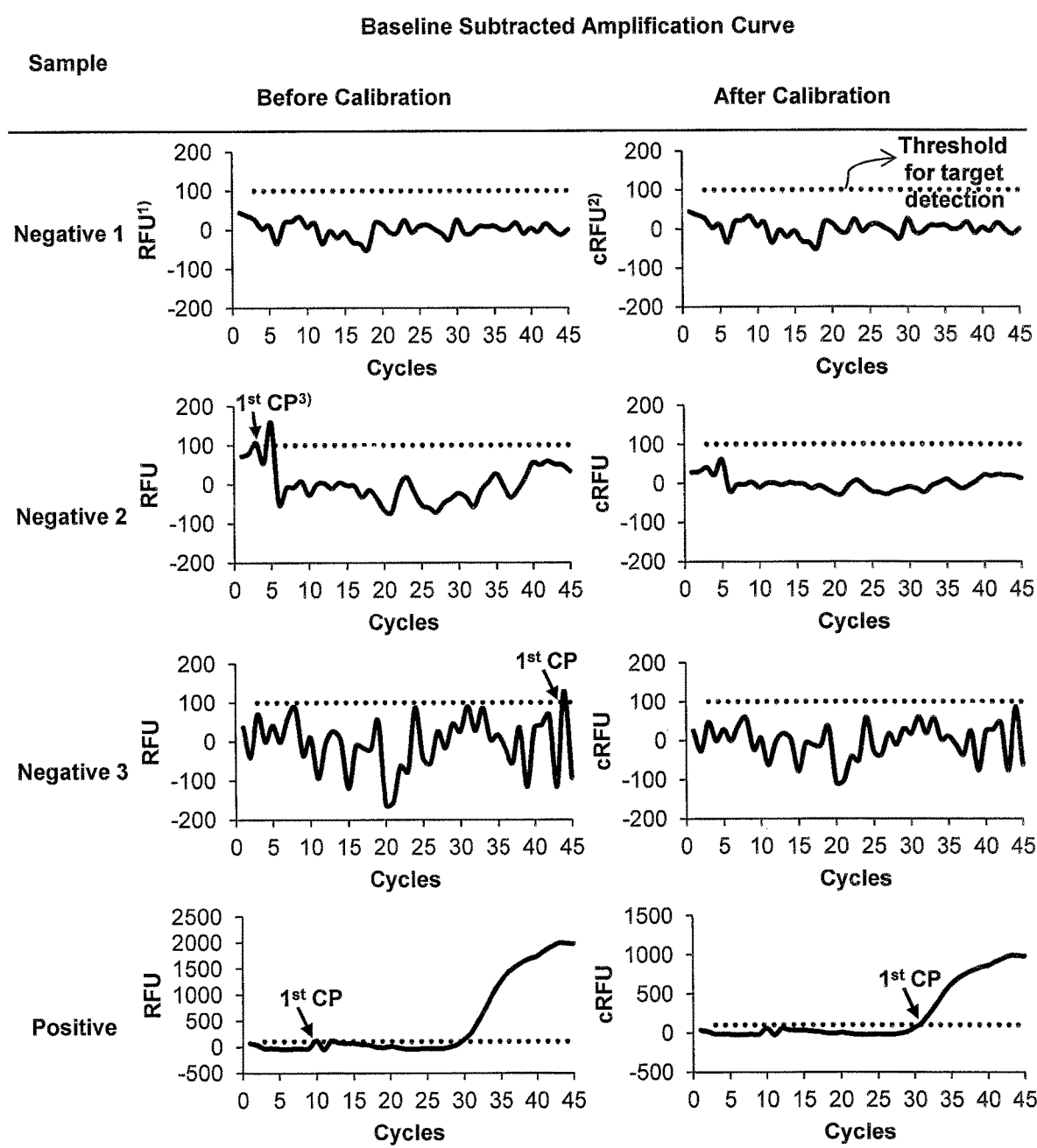
FIG. 6c represents the analysis results of a target nucleic acid molecule before and after the evaluation of the need for the noise reduction and the calibration of the data set using a difference between the maximum and the minimum signal values (ΔRFU) within the noise-level determining region, wherein the noise-reduction determinative value and the noise-reduction goal value are identical.
Figure 6D:
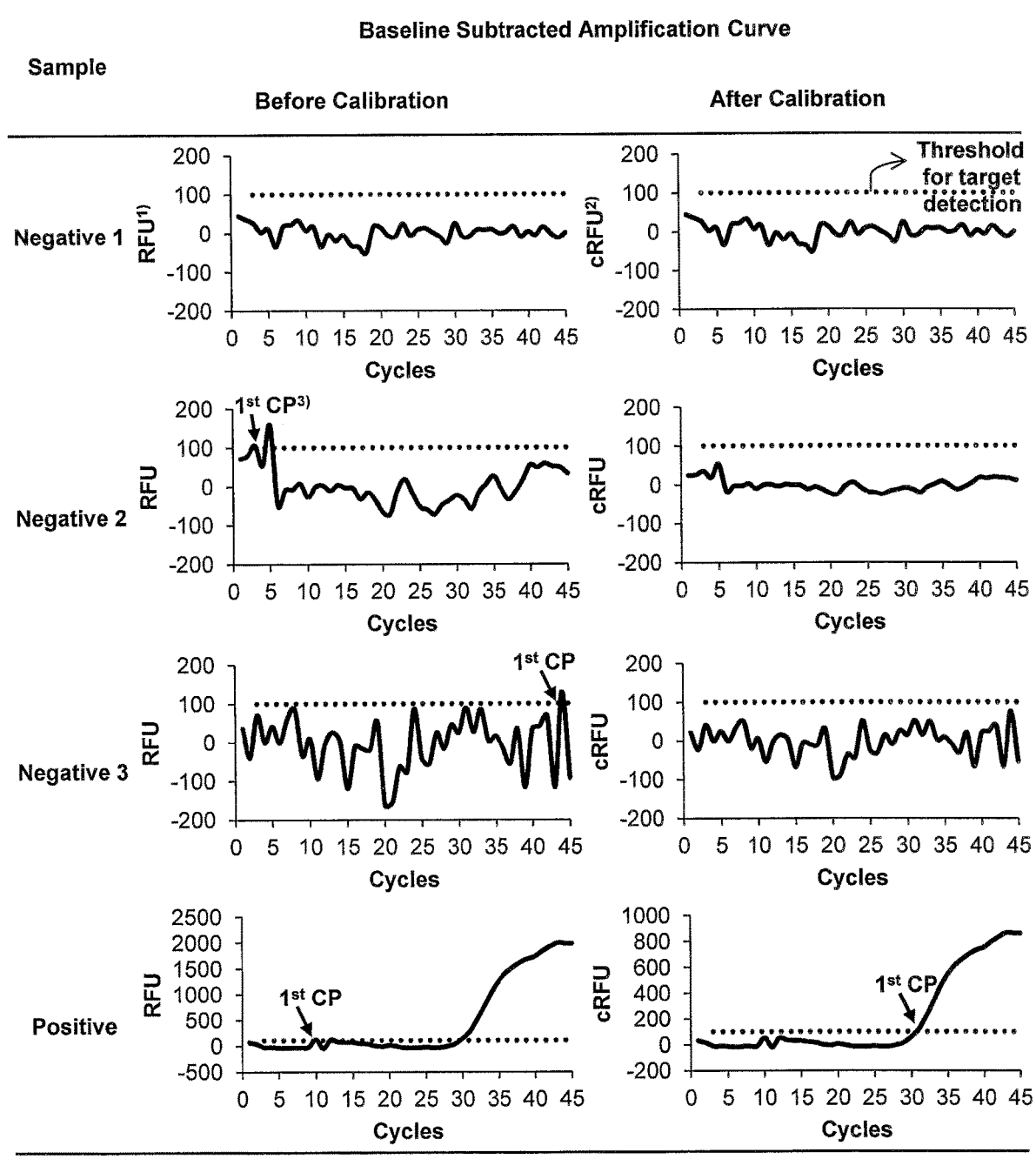
FIG. 6d represents the analysis results of a target nucleic acid molecule before and after the evaluation of the need for the noise reduction and the calibration of the data set using a difference between the maximum and the minimum signal values (ΔRFU) within the noise-level determining region, wherein the noise-reduction goal value is less than the noise-reduction determinative value.

The results of determining the presence of the target nucleic acid and measuring Ct value for the negative samples 1, 2, and 3 and the positive sample were compared between before and after calibration. As shown in FIGS. 6C-6D and Table 6, after calibration, the false positive errors in the negative samples 2 and 3 were corrected and the Ct value error in the positive sample was also calibrated to the correct Ct value. These results demonstrated that the result determination error caused by the abnormally strong background noise signal could be removed by calibrating the data such that the noise level was reduced when the level of background noise signal variation was determined to be deviated from the particular level.

TABLE 6

| Sample | N-GV[1] | T-Th[2] | Before Calibration | | After Calibration | |
|---|---|---|---|---|---|---|
| | | | Ct Value | Determination Result | Ct Value | Determination Result |
| Negative Sample 1 | 80 | 100 | — | Negative | — | Negative |
| Negative Sample 2 | | | 2.77 | False Positive | — | Negative |
| Negative Sample 3 | | | 43.88 | False Positive | — | Negative |
| Positive Sample | | | 9.86 | Positive Ct Value Error | 30.45 | Positive Correct Ct Value |
| Negative Sample 1 | 70 | | — | Negative | — | Negative |
| Negative Sample 2 | | | 2.77 | False Positive | — | Negative |
| Negative Sample 3 | | | 43.88 | False Positive | — | Negative |
| Positive Sample | | | 9.86 | Positive Ct Value Error | 30.67 | Positive Correct Ct Value |

N-GV[1]: Noise-Reduction Goal Value;
T-Th[2]: Threshold for target detection.

<3-2> Calibration of Data Using Maximum Noise Signal

Figure 7A:
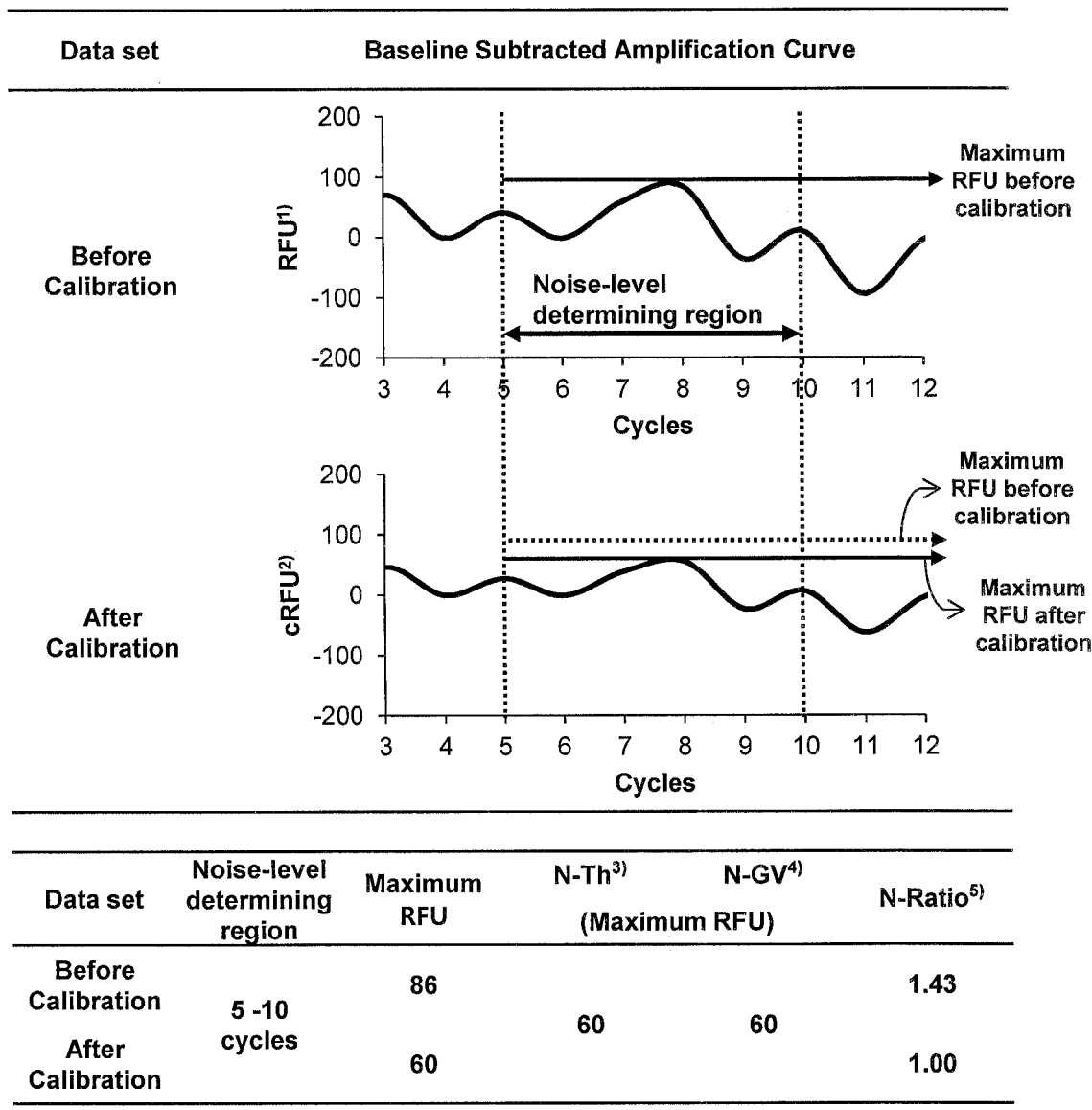
FIG. 7a represents the change of the noise level within the noise-level determining region of the data set generated by evaluating the need for the noise reduction and calibrating the data set using the maximum signal value (Maximum RFU) within the noise-level determining region, wherein the noise-reduction determinative value and the noise-reduction goal value are identical.
Figure 7B:
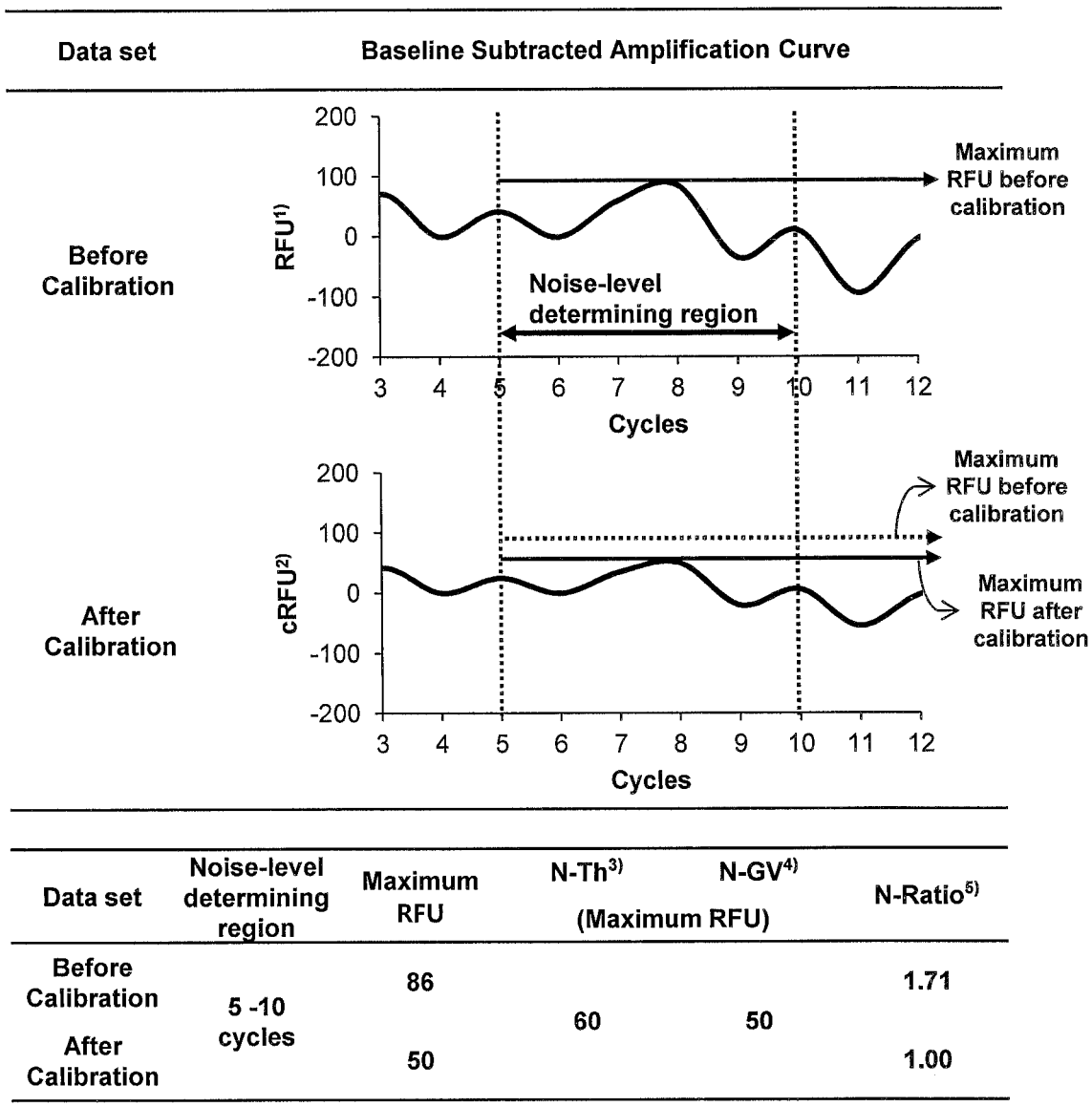
FIG. 7b represents the change of the noise level within the noise-level determining region of the data set by evaluating the need for the noise reduction and calibrating the data set using the maximum signal value (Maximum RFU) within the noise-level determining region, wherein the noise-reduction goal value is less than the noise-reduction determinative value.

As shown in FIGS. 7A-7B, a specific background region was designated as a noise-level determining region in the baseline subtracted amplification curve. After comparing the maximum noise signal (Maximum RFU) in the noise-level determining region with the predetermined noise-reduction determinative value, when the maximum noise signal was equal to or below the noise-reduction determinative value, the data set did not undergo the calibration, whereas when the maximum noise signal was over the noise-reduction determinative value, the data set underwent the calibration.

<Step 1> Designation of Noise Level Determining Region and Determination of Noise Level of Sample As same in Example <2-2>, the region of cycles 5-10 was designated as a noise-level determining region. As a result of determining the noise level of the respective samples, the noise levels of the negative samples 1, 2, and 3 and the positive sample were found to be Maximum RFU 33, Maximum RFU 158, Maximum RFU 86 and Maximum RFU 120 respectively.

<Step 2> Determination of Need for Reduction of Signal Noise Level

The threshold for noise analysis (N-Th) was established as the noise-reduction determinative value for the determination of a need for reduction of the signal noise level. Among many signal values within the noise-level determining region, the signal value, which is to be used as a noise level and compared with the threshold for noise analysis, can be selected in consideration of various conditions. In this example, the maximum signal value (Maximum RFU) within the noise-level determining region of the step 1 was selected as the noise level for the corresponding samples, and then the need for reduction of the signal noise level was determined by comparing the maximum RFU with the threshold for noise analysis. Since the maximum RFU had been designated as the noise level, the threshold for noise analysis could be any value below the threshold for target detection. In this example, the threshold for noise analysis was determined based on the threshold for target detection, i.e. RFU 100 as following:

Threshold for noise analysis (N-Th)=RFU 60 (corresponding to 60% of the threshold for target detection)

The need for reduction of the signal noise level of the data set was determined by comparing the maximum RFU of the step 1 with the threshold for noise analysis determined above. The decision criteria are described below.

Need for reduction of the signal noise level (application of the data calibration): Maximum RFU>N-Th No need for reduction of the signal noise level (no application of the data calibration): Maximum RFU≤N-Th The need for reduction of the signal noise level was determined by using the maximum noise signal. As a result, as shown in Table 7, the maximum signal within the noise-level determining region of the negative sample 1 was calculated as RFU 33, which was below RFU 60 (i.e., threshold for noise analysis) and thus there is no need for reduction of its noise level. On the other hand, the maximum signals of the negative samples 2, 3, and the positive sample were calculated respectively as RFU 158, RFU 86 and RFU 120, which were over RFU 60 (i.e., threshold for noise analysis) and thus there is a need for reduction of their noise levels.

<Step 3> Determination of Noise-Reduction Ratio and Calibration of Data Set

The noise-reduction ratios (N-Ratios) were calculated from the data sets of the negative samples 2 and 3 and the positive sample which had been determined as having a need for reduction of their noise levels. The signal values (RFUs) of the respective cycles were calibrated according to the calculated noise-reduction ratio (N-Ratio).

The noise-reduction goal values were designated in two different manners: (i) the same value as the noise-reduction determinative value; and (ii) the different value from the noise-reduction determinative value.

Noise-reduction goal value 1=ΔRFU 60

Noise-reduction goal value 2=ΔRFU 50

The noise-reduction ratio (N-ratio) was calculated as below:

Noise-reduction ratio (N-Ratio)=maximum RFU÷noise-reduction goal value

As shown in Table 7, when the noise-reduction goal value 1 was used for the calculation of the noise-reduction ratio (N-Ratio), the N-Ratios of the negative samples 2 and 3 and the positive sample were determined as 2.63, 1.43 and 2.00 respectively. Further, when the noise-reduction goal value 2 was used for the calculation of the noise-reduction ratio (N-Ratio), the N-Ratios of the negative samples 2 and 3 and the positive sample were determined as 3.16, 1.71 and 2.40 respectively.

The signal values of the respective cycles of the data sets were calibrated using the respective determined N-Ratios.

The calibrated signal values of the respective cycles of the data sets were determined as below:

The calibrated RFUs of the respective cycles=RFUs of the respective cycles÷N-Ratio The calibrated data sets of the negative samples 2 and 3 and the positive sample were obtained according to the above method.

The noise levels for the obtained calibrated data sets were determined once again through the above steps 1-3. As a result, as shown in Table 7, the noise levels of the calibrated data sets of the negative samples 2, 3 and the positive sample had been reduced to the noise-reduction goal value of ΔRFU 60 or ΔRFU 50. Accordingly, when the noise levels of the calibrated data sets were compared with the noise-reduction determinative value once more, it was found that there was no need for reduction of their noise levels any more.

TABLE 7

| Sample | Data Set | Maximum RFU | N-Th[1] | N-GV[2] | N-Ratio[3] |
|---|---|---|---|---|---|
| Negative Sample 1 | Before Calibration | 33 | 60 | 60 | — |
| | After Calibration | — | | | — |
| Negative Sample 2 | Before Calibration | 158 | | | 2.63 |
| | After Calibration | 60 | | | 1.00 |
| Negative Sample 3 | Before Calibration | 86 | | | 1.43 |
| | After Calibration | 60 | | | 1.00 |
| Positive Sample | Before Calibration | 120 | | | 2.00 |
| | After Calibration | 60 | | | 1.00 |
| Negative Sample 1 | Before Calibration | 33 | | 50 | — |
| | After Calibration | — | | | — |
| Negative Sample 2 | Before Calibration | 158 | | | 3.16 |
| | After Calibration | 50 | | | 1.00 |
| Negative Sample 3 | Before Calibration | 86 | | | 1.71 |
| | After Calibration | 50 | | | 1.00 |
| Positive Sample | Before Calibration | 120 | | | 2.40 |
| | After Calibration | 50 | | | 1.00 |

N-Th[1]: Threshold for Noise Analysis;
N-GV[2]: Noise-Reduction Goal Value;
N-Ratio[3]: Noise-Reduction Ratio.

Figure 7C:
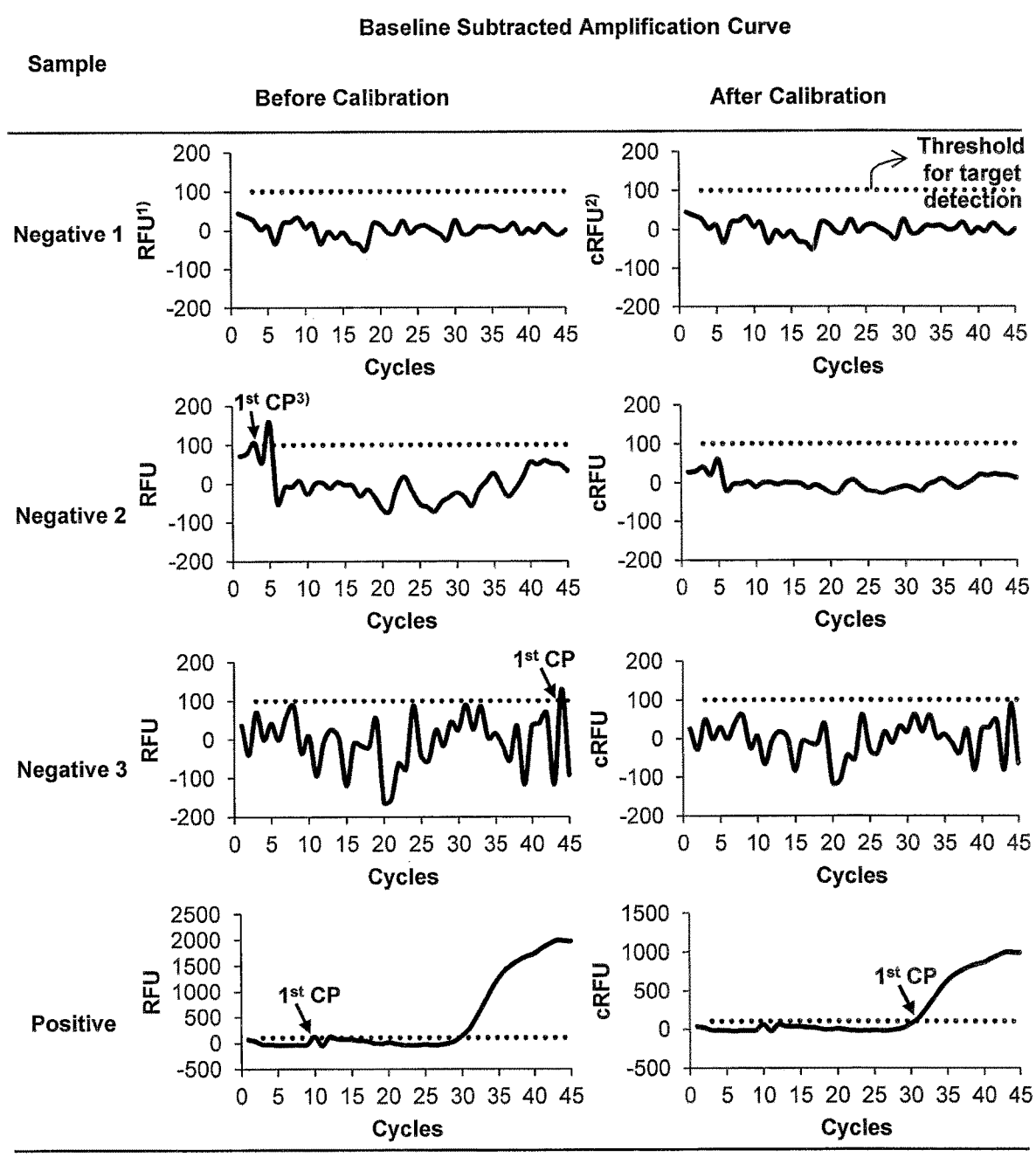
FIG. 7c represents the analysis results of a target analyte before and after the evaluation of the need for the noise reduction and the calibration of the data set using a maximum signal value (Maximum RFU) within the noise-level determining region, wherein the noise-reduction determinative value and noise-reduction goal value are identical.
Figure 7D:
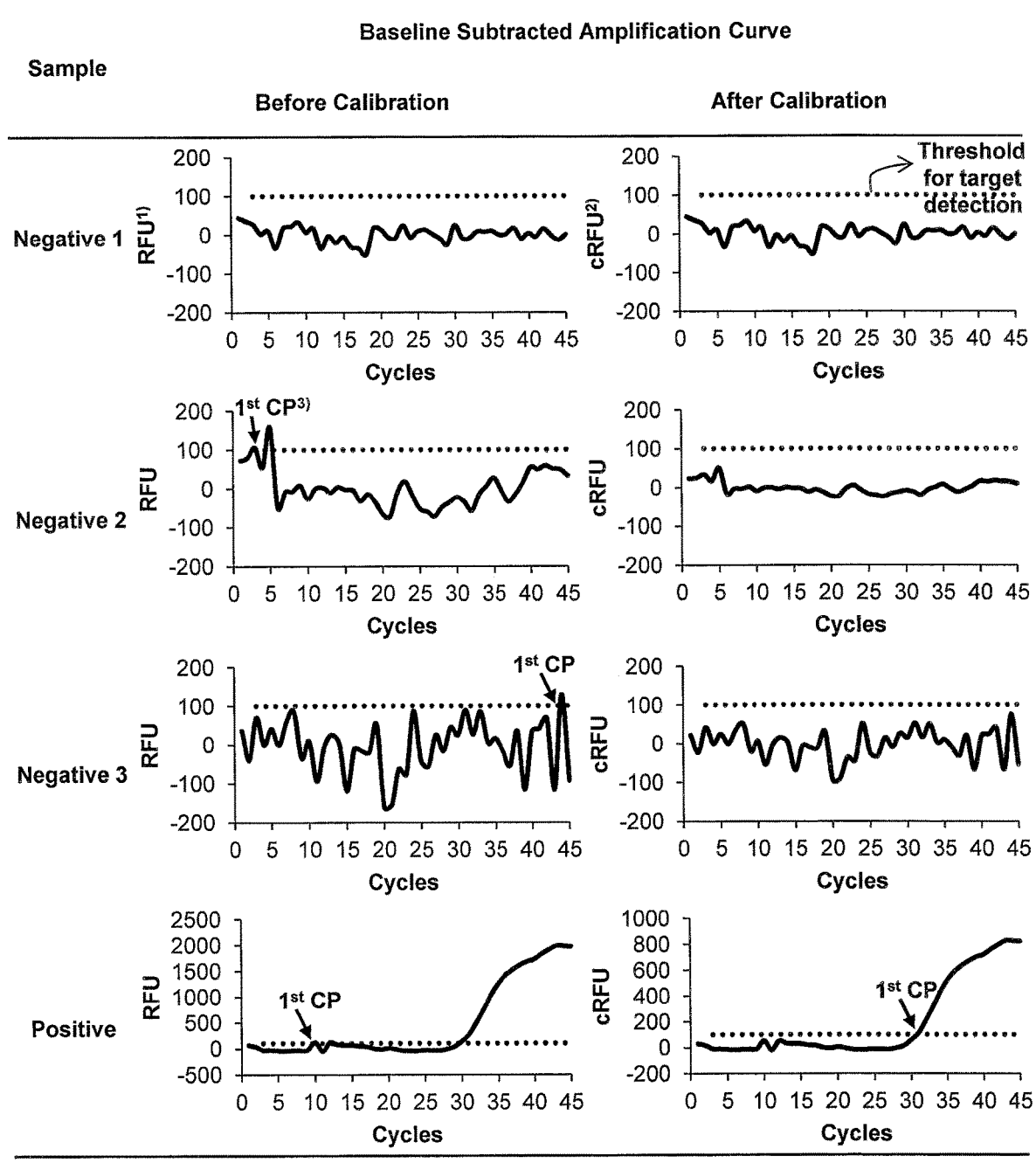
FIG. 7d represents the analysis results of a target nucleic acid molecule before and after the evaluation of the need for the noise reduction and the calibration of the data set using the maximum signal value (Maximum RFU) within the noise-level determining region, wherein the noise-reduction goal value is less than the noise-reduction determinative value.

The results of determining the presence of the target nucleic acid and assessing Ct value for the negative samples 1, 2, and 3 and the positive sample were compared between before and after calibration. As shown in FIGS. 7C-7D and Table 8, after calibration, the false positive errors in the negative samples 2 and 3 had been corrected and the Ct value determination error in the positive sample had been also calibrated to the correct Ct value. These results demonstrated that the result determination error caused by the abnormally strong background noise signal could be removed by calibrating the data such that the noise level was reduced when the background noise signal variation deviates from the particular level.

TABLE 8

| | | | Before Calibration | | After Calibration | |
|---|---|---|---|---|---|---|
| Sample | N-GV[1] | T-Th[2] | Ct Value | Determination Result | Ct Value | Determination Result |
| Negative Sample 1 | 60 | 100 | — | Negative | — | Negative |
| Negative Sample 2 | | | 2.77 | False Positive | — | Negative |
| Negative Sample 3 | | | 43.88 | False Positive | — | Negative |

TABLE 8-continued

| | | | Before Calibration | | After Calibration | |
|---|---|---|---|---|---|---|
| Sample | N-GV[1] | T-Th[2] | Ct Value | Determination Result | Ct Value | Determination Result |
| Positive Sample | | | 9.86 | Positive Ct Value Error | 30.44 | Positive Correct Ct Value |
| Negative Sample 1 | 50 | | — | Negative | — | Negative |
| Negative Sample 2 | | | 2.77 | False Positive | — | Negative |
| Negative Sample 3 | | | 43.88 | False Positive | — | Negative |
| Positive Sample | | | 9.86 | Positive Ct Value Error | 30.74 | Positive Correct Ct Value |

N-GV[1]: Noise-Reduction Goal Value;
T-Th[2]: Threshold for Target Detection.

The above results demonstrate that the method of the present invention is able to remove the errors in determining the presence or absence of the target nucleic acid which are caused by the background noise signal. Moreover, the present method is able to precisely quantify the amplified product of the target nucleic acid.

Furthermore, the present method has the merit such that it can undergo the data calibration after determining whether the reduction of the signal noise is necessary or not thus excluding the unnecessary data calibration. In addition, the present method makes it possible to adjust the range and level of the data calibration because the noise-reduction determinative value can be established differently from the noise-reduction goal value.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for reducing a noise level of a data set for a target analyte in a sample comprising:
    (a) providing a noise-reduction ratio for reducing the noise level of the data set; wherein the data set is obtained from a signal-generating process for the target analyte using a signal-generating means; wherein the data set comprises a plurality of data points comprising cycles of the signal-generating process and signal values at the cycles; wherein the noise-reduction ratio is provided by a value provided by signal values of data points within a noise-level determining region and a noise-reduction goal value; and
    (b) providing a calibrated data set having a reduced noise level by calibrating the signal values of a plurality of data points in the data set with the noise reduction ratio.

2. The method according to claim 1, wherein the noise-reduction ratio is provided by defining a ratio of a maximum value of the signal values of the data points within the noise-level determining region to the noise-reduction goal value.

3. The method according to claim 1, wherein the noise-reduction goal value is a difference between maximum and minimum values within a noise-level determining region of a control data set which is used for determining the noise-reduction goal value; wherein the noise reduction ratio is provided by defining a ratio of (i) the difference between maximum and minimum values within a noise-level determining region of the data set for the target analyte in the sample to (ii) the noise-reduction goal value.

4. The method according to claim 1, wherein the signal-generating process is a process amplifying the signal value; wherein the noise-level determining region is selected within a background region of the data set obtained from the signal-generating process.

5. The method according to claim 1, wherein the noise-reduction ratio is applied to the signal values of a plurality of the data points in the data set with the following mathematical equation 1 such that the calibrated data set having a reduced noise level is provided;

Calibrated signal value of the calibrated data set=signal value of the data set/noise-reduction ratio.    Equation 1:

6. The method according to claim 1, wherein the signal-generating process comprises a plurality of signal-generating processes; wherein the data set comprises a plurality of data sets obtained from the plurality of signal-generating processes.

7. The method according to claim 6, wherein the noise-reduction goal values to be applied to the plurality of data sets are identical to each other.

8. The method according to claim 1, wherein the noise-level determining region comprises one or more cycles.

9. The method according to claim 1, wherein the method further comprises before or after the step (a) the following step:
determining a need for the noise reduction;
(i) by evaluating a noise-level of the data set of the target analyte in a sample and then comparing the noise-level of the data set with a noise-reduction determinative value; or
(ii) by considering the noise-reduction ratio.

10. The method according to claim 9, wherein the noise-level of the data set is determined by using at least one characteristic of signal values of the data points within the noise-level determining region selected from the group consisting of (i) a maximum; (ii) a difference between a maximum and a minimum; (iii) an average; (iv) a variance; (v) a standard deviation; and (vi) a coefficient of variation of signal values of the data points within the noise-level determining region.

11. The method according to claim 9, wherein the noise-reduction determinative value is provided by using a signal value within a noise-level determining region of a control data set obtained from a signal-generating process which is a control signal-generating process for determining the need for the noise reduction.

12. The method according to claim 11, wherein the noise-reduction determinative value is provided by using at least one characteristic of signal values of data points within a noise level determining region of a data set obtained from the control signal-generating process for determining the noise-reduction determinative value selected from the group consisting of (i) a maximum; (ii) a difference between a maximum and a minimum; (iii) an average; (iv) a variance; (v) a standard deviation and (vi) a coefficient of variation of signal values of data points within a noise level determining region of the data set obtained from the control signal-generating process for determining the noise-reduction determinative value.

13. The method according to claim 9, wherein the signal-generating process is a plurality of signal-generating processes; wherein the noise-reduction determinative value is provided by using signal values within the noise-level determining region of at least one data set selected from a plurality of data sets obtained from a plurality of signal-generating processes.

14. The method according to claim 9, wherein the noise-reduction goal value is determined as a value to fulfill a requirement such that when the need for the noise reduction for the calibrated data set having undergone the calibration is evaluated once more after the calibration, the calibrated data set is determined to have no need to further reduce the noise level.

15. A computer readable storage medium containing instructions to configure a processor to perform a method for reducing a noise level of a data set for a target analyte in a sample, the method comprising:
(a) providing a noise-reduction ratio for reducing the noise level of the data set; wherein the data set is obtained from a signal-generating process for the target analyte using a signal-generating means; wherein the data set comprises a plurality of data points comprising cycles of the signal-generating process and signal values at the cycles; wherein the noise-reduction ratio is provided by using a value provided by signal values of data points within a noise-level determining region and a noise-reduction goal value; and
(b) providing a calibrated data set having a reduced noise level by calibrating the signal values of a plurality of data points in the data set with the noise reduction ratio.

* * * * *